United States Patent [19]

Lazzaro et al.

[11] Patent Number: 5,054,494
[45] Date of Patent: Oct. 8, 1991

[54] OSCILLOMETRIC BLOOD PRESSURE DEVICE

[75] Inventors: Gerard M. Lazzaro, Bethlehem; Raymond J. Huey, Stratford, both of Conn.

[73] Assignee: U.S. Medical Corporation, Cheshire, Conn.

[21] Appl. No.: 456,768

[22] Filed: Dec. 26, 1989

[51] Int. Cl.⁵ .............................................. A61B 5/02
[52] U.S. Cl. ..................... 128/677; 128/681; 128/683; 128/687
[58] Field of Search ............... 128/677, 680, 681, 682, 128/683, 687

[56] References Cited

U.S. PATENT DOCUMENTS

| | | | |
|---|---|---|---|
| 3,315,662 | 4/1967 | Buffington | 128/681 |
| 3,738,356 | 6/1973 | Workman | 28/675 |
| 3,765,405 | 10/1973 | Natkanski | 128/680 |
| 3,894,535 | 7/1975 | Cannon et al. | 128/672 |
| 4,137,907 | 2/1979 | Jansen et al. | 128/681 |
| 4,154,238 | 5/1979 | Link | 128/681 |
| 4,159,111 | 6/1979 | Lowth | 128/25 |
| 4,206,765 | 6/1980 | Huber | 128/677 |
| 4,211,238 | 7/1980 | Shu et al. | 128/700 |
| 4,216,779 | 8/1980 | Squires et al. | 128/682 |
| 4,252,127 | 2/1981 | Gemelke | 128/680 |
| 4,258,430 | 3/1981 | Tyburski | 364/900 |
| 4,263,918 | 4/1981 | Swearingen et al. | 128/681 |
| 4,326,569 | 4/1982 | Vaillancourt | 141/383 |
| 4,344,421 | 8/1982 | Bareiss | 28/24 |
| 4,356,827 | 11/1982 | Uemura et al. | 128/680 |
| 4,361,877 | 11/1982 | Dyer et al. | 364/900 |
| 4,378,807 | 4/1983 | Peterson et al. | 128/680 |
| 4,400,783 | 8/1983 | Locke, Jr. et al. | 364/483 |
| 4,407,297 | 10/1983 | Croslin | 128/681 |
| 4,417,306 | 11/1983 | Citron et al. | 364/415 |
| 4,417,587 | 11/1983 | Ichinomiya et al. | 128/682 |
| 4,420,819 | 12/1983 | Price et al. | 364/900 |
| 4,429,700 | 2/1984 | Thees et al. | 128/681 |
| 4,461,266 | 7/1984 | Hood, Jr. et al. | 128/681 |
| 4,464,123 | 8/1984 | Glover et al. | 128/681 |
| 4,466,879 | 8/1984 | Ho et al. | 204/415 |
| 4,501,280 | 2/1985 | Hood, Jr. | 128/677 |
| 4,519,398 | 5/1985 | Lisiecki et al. | 128/710 |
| 4,543,963 | 10/1985 | Medero et al. | 128/682 |
| 4,546,775 | 10/1985 | Medero | 128/681 |
| 4,576,180 | 3/1986 | Taheri | 128/673 |
| 4,592,018 | 5/1986 | Wiegman | 365/63 |
| 4,592,366 | 6/1986 | Sainomoto et al. | 128/680 |
| 4,608,994 | 9/1986 | Ozawa et al. | 128/670 |
| 4,617,937 | 10/1986 | Peel et al. | 128/680 |
| 4,618,929 | 10/1986 | Miller et al. | 364/415 |
| 4,627,440 | 12/1986 | Ramsey, III et al. | 128/682 |
| 4,634,982 | 1/1987 | Pungor et al. | 324/448 |
| 4,638,810 | 1/1987 | Ramsey, III et al. | 128/681 |
| 4,653,506 | 3/1987 | Romanovskaya | 28/685 |
| 4,660,566 | 4/1987 | Palti | 128/677 |
| 4,677,983 | 7/1987 | Yamaguchi et al. | 128/680 |
| 4,690,151 | 9/1987 | Utsunomiya et al. | 128/682 |
| 4,699,152 | 10/1987 | Link | 128/677 |
| 4,706,684 | 11/1977 | Sorensen et al. | 128/677 |
| 4,712,563 | 12/1987 | Link | 128/681 |
| 4,712,564 | 12/1987 | Yamaguchi | 128/682 |
| 4,716,906 | 1/1988 | Ruff | 128/686 |
| 4,717,885 | 3/1988 | Ruff | 128/686 |

(List continued on next page.)

Primary Examiner—Francis Jaworski
Assistant Examiner—George Manuel
Attorney, Agent, or Firm—Varnum, Riddering, Schmidt & Howlett

[57] ABSTRACT

An oscillometric blood pressure measuring device (200) is disclosed for determining systolic, mean and diastolic blood pressures. The device (200) includes a cuff (202) adapted to be continuously deflated during a measuring cycle. Analog signals representative of pulsatile changes in cuff pressure are utilized to generate signals representative of pulse characteristics, including peak amplitude and pulse integral characteristics. Difference signals are then generated for the pulses, representative of the difference between peak amplitudes and pulse integrals, and a determination is made as to the systolic and diastolic blood pressure based on these difference signals and static cuff pressures.

33 Claims, 10 Drawing Sheets

U.S. PATENT DOCUMENTS

| | | | |
|---|---|---|---|
| 4,718,426 | 1/1988 | Russell | 128/679 |
| 4,718,427 | 1/1988 | Russell | 128/679 |
| 4,718,428 | 1/1988 | Russell | 128/679 |
| 4,722,349 | 2/1988 | Baumberg | 128/677 |
| 4,723,555 | 2/1988 | Shue | 128/715 |
| 4,729,382 | 3/1988 | Schaffer et al. | 128/679 |
| 4,729,383 | 3/1988 | Susi | 128/680 |
| 4,729,385 | 3/1988 | Juncosa et al. | 128/734 |
| 4,730,621 | 3/1988 | Stott | 128/687 |
| 4,735,213 | 4/1988 | Shirasaki | 128/681 |
| 4,737,884 | 4/1988 | Wada et al. | 361/392 |
| 4,745,924 | 5/1988 | Ruff | 128/686 |
| 4,747,412 | 5/1988 | Yamaguchi | 128/683 |
| 4,751,930 | 6/1988 | Tereda et al. | 128/681 |
| 4,754,401 | 6/1988 | Kaczynski et al. | 364/413 |
| 4,754,406 | 6/1988 | Miyawaki et al. | 364/416 |
| 4,754,761 | 7/1988 | Ramsey, III et al. | 128/683 |
| 4,768,518 | 9/1988 | Peltonen | 128/677 |
| 4,768,519 | 9/1988 | Yamaguchi | 128/680 |
| 4,774,960 | 10/1988 | Arnold et al. | 128/681 |
| 4,776,344 | 10/1988 | Shirasaki et al. | 128/681 |
| 4,777,959 | 10/1988 | Wallach et al. | 128/677 |
| 4,779,626 | 10/1988 | Peel et al. | 128/675 |
| 4,785,820 | 11/1988 | Brooks | 128/681 |
| 4,790,325 | 12/1988 | Lee | 128/677 |
| 4,793,360 | 12/1988 | Miyawaki et al. | 128/681 |
| 4,796,184 | 1/1989 | Bahr et al. | 364/413.03 |
| 4,799,492 | 1/1989 | Nelson | 128/672 |
| 4,800,892 | 1/1989 | Perry et al. | 128/677 |
| 4,819,654 | 4/1989 | Weaver et al. | 128/680 |
| 4,821,734 | 4/1989 | Koshino | 128/680 |
| 4,830,018 | 5/1989 | Treatch | 128/677 |
| 4,832,039 | 5/1989 | Perry et al. | 128/680 |
| 4,832,040 | 5/1989 | Ruff | 128/686 |
| 4,844,306 | 7/1989 | Ruff et al. | 224/202 |
| 4,889,132 | 12/1989 | Hutcheson et al. | 128/680 |
| 4,889,133 | 12/1989 | Nelson et al. | 128/681 |
| 4,890,625 | 1/1990 | Sorensen | 128/680 |
| 4,896,676 | 1/1990 | Sasaki | 128/681 |
| 4,898,180 | 2/1990 | Farrelly et al. | 128/681 |
| 4,949,710 | 8/1990 | Dorsett et al. | 128/681 |

BLOCK DIAGRAM
MICROPROCESSOR

BLOCK DIAGRAM
MICROCOMPUTER

OSCILLOMETRIC BLOOD PRESSURE DEVICE

BACKGROUND OF THE INVENTION

1. Field of the Invention

The present invention relates to apparatus and methods for measuring blood pressure and, in particular, relates to apparatus and methods for determining systolic, diastolic and mean arterial pressures by employing oscillometric techniques and analyzing electrical signals detected by a pressure transducer representative of pressures.

2. Description of Related Art

It is relatively well known in the art of blood pressure measurement design that the orderly depolarization of the heart muscle triggers a wave of contraction which "spreads" through the walls of the chamber of the heart containing the musculature that acts during the pumping of blood, i.e. the myocardium. The contraction process actually produces the pumping action, by sequentially changing the pressure (and, therefore, blood flow) in the heart chambers and blood vessels. However, primarily because of the elastic properties of the blood vessels in the arterial system, and the discontinuous nature of myocardial contraction which produces ejection of blood from the ventricles, the precise relationship between arterial blood pressure and blood flow is relatively complex. In addition, the discontinuous pumping action of the heart is opposed by the impedance of the arterial system.

The radial stretch of the aorta resulting from left ventricular ejection initiates a pressure "wave" which propagates down the aorta and the arterial blood vessels. The arterial pressure waveform becomes relatively progressively more distorted as the wave is transmitted down the arterial system. This distortion may be attributed to the impedance of the arterial system. The impedance of the arterial system can be affected by a number of factors, including: (1) characteristics of blood; (2) the viscoelastic characteristics of the arteries; (3) arterial capacitance; (4) "tapering" of the lumen of blood vessels; (5) resonance; (6) reflected pressure waves due to arterial branching, and changes in transmission velocity with pressure. Notwithstanding the foregoing, arterial blood pressure is a quantitative measurement routinely obtained in a variety of known ways for purposes of diagnosis of patients.

Arterial blood pressure is generally expressed in terms of systolic and diastolic pressures. These pressures are, respectively, upper and lower limits of period oscillations about a mean arterial blood pressure. Systolic pressure is typically measured when, during left ventricular ejection, a volume of blood is relatively rapidly introduced into the arterial system, initially into the aorta. A "maximum" arterial blood volume is reached at the end of this rapid ejection phase (commonly referred to as the early part of systole) which corresponds to a peak pressure defined as systolic pressure. Correspondingly, diastolic pressure is typically measured in the absence of ventricular ejection of blood; that is, when all four chambers of the heart are relaxed (i.e. diastole). This measurement typically occurs immediately prior to the next ventricular ejection. The lowest pressure obtained during diastole is characteristically defined as diastolic pressure.

As a graphical illustration of the events which occur in the heart and relate to blood pressure, FIG. 1 depicts certain blood pressure-related waveforms as a function of time. Referring specifically to FIG. 1, changes in aortic pressure are represented by aortic pressure waveform 100. As apparent from waveform 100, during ventricular systole, the ejection of blood from the left ventricle is initially relatively rapid. As the rate of pressure change decreases during systole, the maximum aortic pressure is obtained. Correspondingly, when the systolic period is completed, the aortic valve is closed by the back pressure of blood against the valve. This effect is illustrated in FIG. 1 as the dicrotic notch 102 of the aortic pressure waveform 100.

Also illustrated in FIG. 1 is arterial blood pressure waveform 104 representative of the blood pressure within a peripheral artery. With respect to the blood pressure waveform 104, a dicrotic notch 106 is illustrated, corresponding to the effect on the arterial blood pressure waveform of the completion of the systolic period resulting from the closing of the aortic valve by the blood back pressure against the valve. When the aortic valve is completely closed, the aortic pressure gradually decreases as blood pours into the arterial system, thereby producing blood pressure pulses, such as arterial blood pressure pulse 108. Correspondingly, the left ventricular pressure, illustrated in FIG. 1 as left ventricular pressure waveform 110, also gradually decreases until the left ventricle again begins to fill with blood in preparation for the next systolic period. This action will result in the arterial blood pressure pulse illustrated as arterial blood pressure pulse 112 on the wave form 104. The overall shape of each arterial blood pressure pulse will change, as each pulse passes through the arterial system. However, a dicrotic notch will always be present with respect to the pulses.

A number of devices are relatively well known for obtaining blood pressure measurements of a test subject. The most common form of blood pressure measurement employs indirect measurement techniques utilizing a compression bag or "pressure cuff" for the application of external pressure to an artery. Typically, this cuff is a pneumatic cuff adapted to encircle the upper arm of a test subject.

The most common form of blood pressure measuring device also employs a hand pump and pressure gauge. These devices are often referred to as sphygmomanometers. With these devices, an inflatable section of the cuff is inflated by a small hand pump and the cuff pressure is indicated by a mechanical pressure gauge or a manometer calibrated in terms of millimeters of mercury. The cuff is typically inflated to a pressure greater than the systolic blood pressure in the large brachial artery of the arm. This pressure essentially "collapses" a segment of the artery under the cuff, and occludes the blood flow through the artery.

After cuff inflation, the pressure in the cuff is typically allowed to decrease. This decrease is often achieved through the use of a release valve built into the hand pump. During pressure decrease, a pressure level is reached where the cuff pressure and the peak or systolic arterial pressure are substantially equal. At a pressure slightly below this cuff pressure level, the peak arterial pressure slightly exceeds the cuff pressure and blood first begins to flow or "squirt" through the compressed segment of the brachial artery.

This flowing or squirting blood will result in turbulence within the brachial artery, thereby creating sounds referred to as Korotkoff sounds. Auscultatory techniques are usually employed to determine the systolic and diastolic pressures based on the Korotkoff sounds. For example, it is typical to detect these sounds with a stethoscope placed over the brachial artery distal to the cuff.

As the pressure in the cuff is further decreased, Korotkoff sounds continue until a point is reached where no further turbulence is produced, since the brachial artery segment may then be just slightly constricted. This cuff pressure represents the diastolic blood pressure.

Although this technique, employing auscultatory methods for detecting Korotkoff sounds, is the most common type of blood pressure device currently available, these types of devices suffer from several disadvantages. Of primary importance, it is relatively difficult to detect the pressure where the Korotkoff sounds begin and where they cease, due to the interpretative nature of the measure. Accordingly, it is difficult, using auscultatory techniques, to provide an accuracy greater than approximately five millimeters of mercury.

Various techniques are also known for automating auscultatory devices. For example, the hand pump of the typical device may be replaced with an automatic cuff pump. The automatic cuff pump may be operated by utilizing a panel-mounted button to produce a single cycle of inflation and deflation or, alternatively, repetitive cycles at various intervals for continuous monitoring of blood pressure over relatively long periods of time may be provided. In addition, the stethoscope may be replaced by a Korotkoff-sound microphone, consisting of a relatively small piezoelectric transducer specially designed for accurate reproduction of Korotkoff sounds. Still further, the pressure gauge may also be replaced with a pressure transducer, similar to transducers utilized for direct measurement of blood pressure.

For providing further automation, the indirect blood pressure may be recorded, utilizing electronic apparatus, thereby somewhat increasing the accuracy of the auscultatory method. That is, such recording will somewhat remove human judgment in determining the presence of the Korotkoff sounds.

Further, the auscultatory techniques are relatively susceptible to false indications caused, for instance, by motion artifacts and ambient noise. In addition, the cuff must be substantially at heart level, to obtain a pressure relatively uninfluenced by gravity. Other problems can exist with respect to the actual physiology of the test subjects. For example, with individual test subjects having relatively obese arms, the body fat in the arm can somewhat dissipate some of the cuff pressure, such that pressure measurements are erroneously high. Still further, if the cuff is left inflated for some time, discomfort may cause generalized reflex vasoconstriction, thereby raising the blood pressure.

Still further, if an electronic unit is utilized to interpret output from a pressure transducer, correct positioning of the sound microphone over the brachial artery is critical. In addition, it has been found, based on direct and indirect blood pressure measurements made simultaneously, that diastolic pressure tends to correlate better with the cuff pressure at which the sounds become muffled, rather than with the pressure at which the sounds disappear (i.e. when turbulence ceases). Accordingly, the particular cuff pressure at which Korotkoff sounds tend to cease does not appear to be an important criteria in determining the actual diastolic blood pressure.

Various types of blood pressure measurement devices employing auscultatory techniques are shown in a number of patent references, including: Squires et al, U.S. Pat. No. 4,216,779; Gemelke, U.S. Pat. No. 4,252,127; Uemura, U.S. Pat. No. 4,356,827; Peterson, U.S. Pat. No. 4,378,807; Ichinomiya et al, U.S. Pat. No. 4,417,587; Sainomoto et al, U.S. Pat. No. 4,592,366; and Peel et al, U.S. Pat. No. 4,617,937.

Another method employed for blood pressure measurement techniques, and the method most relevant to the present invention, is typically referred to as an oscillometric or oscillatory method. Oscillometric blood pressure measuring devices essentially comprise analysis of electrical signals related to the blood pressure waveform. In many oscillometric devices, a pneumatic cuff is implemented substantially as previously described with respect to devices employing auscultatory techniques. However, in most oscillometric methods, a single pressure transducer is employed to detect both cuff pressures and pulsating pressures, resulting from periodic changes in pressure in the blood vessel. These pressure transducers convert the pressure detections into proportional electrical signals. These signals are then analyzed and processed for determining, from the pulsating pressures, the cuff pressures corresponding to the systolic and diastolic blood pressures. The signals representative of the pulsating pressures can also be utilized for determining other blood pressure characteristics, such as the mean arterial pressure.

A substantial number of oscillometric blood pressure measuring systems are currently known. A number of these systems comprise oscillometric blood pressure measuring devices utilizing a pressure transducer for converting cuff and pulse pressures into electrical signals. Various hardware circuitry and/or computer software can be employed to analyze "characteristics" of the pulses. For example, various known systems employ electrical and electronic devices for analyzing characteristics such as pulse height, pulse width and the like. Many of the inventions claimed in patent references directed to oscillometric systems are specifically directed to the pulse analysis techniques for making a determination of the relevant blood pressures.

With respect to the various known oscillometric blood pressure measuring systems, several potential problems are known. For example, blood pressure pulses superimposed on the occluding pressures are typically relatively small in height. Accordingly, it is somewhat difficult to detect the pulsating pressures within signals representative of the cuff pressures. Further, even relatively slight movements of the test subject during a measurement cycle can result in "false" pulse representations within the transducer output signals. Such false pulses are often characterized as "artifacts." Such pulses artifacts can be caused not only by the test subject's movement of the arm comprising the measured artery, but can also be caused merely by the slight movements associated with respiration. A number of other reasons also exist for artifact generation.

Again, the disadvantages associated with artifact generations and oscillometric measuring systems are relatively well known. The pulse analysis techniques described in many patent references are specifically directed to discriminating between true pressure pulsations and artifact pulse representations, and minimizing erroneous blood pressure determinations resulting from the artifacts.

An example of a blood pressure measuring device employing oscillometric techniques for determining systolic and diastolic blood pressures is disclosed in the U.S. Pat. No. 4,407,297 issued to Croslin and dated Oct. 4, 1983. As disclosed in the Croslin patent, after an artery is occluded by inflating a pneumatic cuff in the usual manner, four successive pulses must be detected as the pressure in the cuff is permitted to decrease at a rate less than 10 mm HG between successive pulses. That is, an error is considered to have occurred if the difference between a pulse and the preceding pulse is at least 10 mm HG. Also, an error is considered to have occurred if more or less than four pulses are detected when the cuff pressure deflates to 30 mm HG. For each detected pulse, two data items characterizing each pulse are stored in a table in memory. The first data item stored for each pulse is the cuff pressure detected at the start of the pulse. A second data item is the maximum amplitude of the pulse. A pulse is assumed to have occurred when a maximum amplitude is at least equivalent to 1 mm HG. However, when the value of the pulse amplitude is greater than a predetermined value, the pulse is assumed to be too large, and the measurement cycle is aborted.

Pulses are counted within a 10-second time interval, beginning with the detection of the third pulse. A 3-second time interval begins after the 10-second time interval times out. At least one pulse must be detected during the 3-second interval. If the sequence of pulses is considered valid, the cuff pressure detected at the start of a predetermined pulse is characterized as the systolic pressure. Diastolic pressure is determined to have occurred when the average of the amplitudes of four pulses is less than a predetermined threshold value, calculated as a function of the detected mean arterial pressure. In summary, if the amplitude of a pulse exceeds the previous pulse amplitude by more than 1 mm HG, or if the cuff pressure has decreased by at least 10 mm HG between successive pulses, an artifact is assumed to have been detected, unless four successive pulses have been previously detected for determining systolic blood pressure.

In another arrangement, as disclosed in U.S. Pat. No. 4,263,918 issued to Swearingen et al and dated Apr. 28, 1981, a somewhat different pulse analysis is undertaken. Again, a transducer provides a signal which is separated into a signal representative of static cuff pressure and a signal representative of pulsatile pressure in the cuff resulting in changes in arterial blood pressure. A comparator determines the start of each pulsatile signal, and produces a control signal when the pulse amplitude exceeds a predetermined reference value. The cuff pressures associated with the pulsatile signals are stored in a cuff pressure table in digital memory. Six of the "highest amplitude" pulses are also stored in a pulse table memory.

Of the six stored pulse amplitudes, the three pulses having the largest amplitudes, although not necessarily adjacent to one another in the table, are selected. That is, the pulse having a maximum height is selected, as well as two other pulses closest thereto in amplitude.

The Swearingen et al technique utilizes an algorithm whereby the pulses in the table are examined until a three-pulse set is detected, wherein the pulse having maximum height is less than or equal to 125 percent of the smallest of the other two pulses. When detected, the average of these three largest amplitude pulses is utilized as a reference level.

For purposes of obtaining systolic blood pressure, a level of 45 percent of the reference level is utilized. The system then searches upward in the pulse table, in the direction of higher cuff pressures from one of the six highest amplitude pulses, until another set of three pulses is found whereby two of these three pulses are each less than the systolic threshold level, and the third of these three pulses is greater than or equal to the systolic threshold level. The third pulse must be detected adjacent to the other two pulses, but closest to the single-highest amplitude pulse from which the search was initiated. The address of this third pulse in the pulse table is utilized as a pointer to the corresponding cuff pressure in the cuff pressure table. This cuff pressure is characterized as the systolic blood pressure.

For purposes of obtaining diastolic blood pressure, a diastolic threshold level is determined as 75 percent of the reference level. The algorithm then searches downward in the pulse table in the direction of lower cuff pressures, from the same one of the six highest amplitude pulses until another set of three pulses is found, whereby two of these three pulses are each less than the diastolic threshold level, and the third of these three pulses is greater than or equal to the diastolic threshold level. This third pulse must be adjacent to the other pulses, but closest to the one highest amplitude pulse from which the search was initiated. The address of this third pulse in the pulse table is utilized as a pointer to the corresponding cuff pressure in the cuff pressure table. This cuff pressure is characterized as the diastolic blood pressure.

In the Swearingen et al system, an error is considered to have occurred if the systolic pressure is not greater than the sum of diastolic pressure, plus 10 mm HG. Each of the cuff pressures is determined by subtracting a zero pressure offset, representing at least 2 mm HG, from static cuff pressure. For purposes of attempting to insure accuracy, a minimum number of 16 pulses must be obtained, at a cuff "bleed" rate of 3 to 6 mm HG per beat. At least 10 pulse amplitudes must be stored in the pulse table (in the direction of lower cuff pressure) beyond the predetermined highest amplitude pulse from which the previously described searches were initiated.

The ten pulses are utilized to assure that pulses are available after the occurrence of any "gap." To further improve accuracy, the concept is utilized that if the lowest amplitude pulse in the group of six highest amplitude pulses is less than or equal to a predetermined number, or greater than the predetermined number and less than or equal to a second predetermined number, or otherwise greater than the second predetermined number, a "stop measurement" cuff pressure is provided at either 75 mm HG, 85 mm HG or 120 mm HG, respectively. Accordingly, if the very last pulse table is greater than the applicable "stop measurement" cuff pressure, additional pulse pressures are acquired by the system. Otherwise, the worst case peak average reference is obtained from the three lowest pulse amplitudes of the set of six highest pulse amplitudes, and is characterized as 25 percent of the sum of the three lowest of the six highest pulse amplitudes. This worst case peak average reference would be less than or equal to any diastolic threshold level then currently determined. If two pulses are found by the system (in the manner previously described with respect to obtaining diastolic pressure) having amplitudes less than the worst case peak average, diastolic blood pressure is obtained. If two such pulses cannot be found, the system will acquire additional data, but the next pulse must be acquired within 1.8 seconds.

For purposes of discriminating true pulses from artifacts, the pulse amplitudes, in the pulse table, next adjacent or two away (on either side) from the largest pulse must be greater than or equal to 66 percent of the largest pulse. If artifacts are detected, the system continues to find the set of three highest pulses and the set of six largest pulses in the pulse table, meeting the appropriate criteria.

Again, a primary emphasis of a number of the patent references directed to oscillometric blood pressure measuring devices is the discrimination of artifacts versus true pulses, and resulting minimization of erroneous blood pressure measurements. As also previously described, various pulse characteristics are employed by several known systems, for purposes of accurately determining the relevant blood pressure levels. Although a number of these references primarily concentrate on characteristics such as pulse height, other characteristics can also be analyzed.

For example, U.S. Pat. No. 4,751,930, issued to Terada et al and dated June 21, 1988, is directed a pulse analysis arrangement utilizing pulse characteristics derived as functions of the pulse integrals. As disclosed, the Terada et al system includes a conventional occluding cuff coupled through a tube to a pressure transducer. The pressure transducer is mounted to an apparatus having associated electronics. The electronics include a low-pass filter, analog/digital (A/D) converter and microcomputer. Resultant blood pressure measurements are provided to a display.

The output signal from the transducer, representing both the "static" cuff pressure and the arterial blood pressure, is applied as an input signal to the A/D converter. The A/D converter samples the analog signal for providing discrete digital signals applied to the microcomputer. The microcomputer includes software functions for extracting, from the sampled cuff pressure data, a "pulsating quantity" representative of each blood pressure pulse occurring in sequence. Also included in the functions of the microcomputer is the feature of extracting the static cuff pressure from the sampled cuff pressure data.

In the Terada et al patent, the "pulsating quantity" is specifically described as being an integral or a function of an integral of the blood pressure pulse superimposed upon the static cuff pressure. For purposes of deriving this pulsating quantity, the Terada et al system measures data which includes the pressure level at the onset of a pulse. Also measured is the time of the onset of the pulse, the pressure level at the peak of the pulse, and the time of occurrence of the pulse peak.

For purposes of determining the pressure level at the onset of the pulse, the microcomputer senses when the actual pressure increases relative to the pressure measured during the last time interval. If such an increase occurs, and if such an increase is maintained over a predetermined time interval, the pressure level at the onset of the pulse is assumed to have occurred. Correspondingly, the time of occurrence is also obtained. The peak of the pulse pressure, in addition to the time of occurrence of the peak, is obtained in a similar manner, i.e. by determining when the increase in cuff pressure begins to decrease.

The Terada et al patent also discloses various arrangements for obtaining the pulsating quantity in terms of the integral of the pulse. One such arrangement is a computation of the total area under the pulse "curve" above a base pressure at the onset of the pulse. This integral value is obtained for each of the pulses, and is essentially "plotted" with respect to time. Correspondingly, the microcomputer also keeps track of the static cuff pressures at the onset of the pulses.

In another method described in the Terada et al patent, instead of obtaining the total area under the pulse curve above the onset base pressure for each pulse, the pulsating quantity can be computed as the area of the region bounded by the pulse curve between the onset time and the peak time, above the onset base pressure level. That is, the area of the pulse utilized is only that area above the onset base pressure level and up until the time of the pulse peak. This arrangement is described as being preferable, since the complutation of the integral of the pulse beyond the pulse peak may fluctuate, depending upon the bleed rate of the cuff pressure. This type of integral measurement is further characterized within the patent as providing a more consistent analysis of the pulses, resulting in relatively more reliable determinations of the blood pressure measurements.

Further, the Terada et al patent additionally describes the concept that the pulsating quantity can be defined as a quotient of an integral of the pulse, divided by a particular value of time within the time period of the pulse. In other words, the pulsating quantity would be an average pressure level during a pulse (above the onset value) obtained by dividing the integral of the pulse by the particular time width.

In the Terada et al system, and a number of other oscillometric blood pressure measuring systems currently known, sampling of instantaneous cuff pressures typically is performed at a rate which is substantially more frequent than the rate of blood pressure pulses. In addition, within such systems, sampling is continuously performed during the generation of a pulse, so as to determine various pulse characteristics. Also, in a number of the currently-known systems, the determination of systolic, diastolic and mean arterial blood pressures is typically performed in a "batch" type mode. That is, sampled data is obtained throughout the cuff deflation cycle from a pressure above systolic blood pressure to a pressure below diastolic blood pressure. During this pressure deflation interval, data is stored with respect to each detected pulse, including pulse characteristics and static cuff pressures associated with the occurrences of the pulses. After the entire pressure deflation cycle is completed, the stored data is utilized to analyze the pulse characteristics of the pulses and to determine systolic, diastolic and mean blood pressures.

SUMMARY OF THE INVENTION

In accordance with the invention, an oscillometric blood pressure device for measuring systolic and diastolic blood pressures is adapted to be interconnected to a cuff attachable to a test subject. The device includes means adapted to be coupled to the cuff for applying an occluding pressure greater than the systolic pressure in the vicinity of an artery of the test subject. Means are also provided which are adapted to be coupled to the cuff for decreasing the occluding pressure to a pressure below the diastolic pressure. A pressure transducer, also adapted to be coupled to the cuff, generates analog pressure signals representative of instantaneous cuff pressure. The analog pressure signals include a first analog signal representative of blood pressure pulses occurring in the artery, and a second analog signal representative of static cuff pressure.

Further in accordance with the invention, circuit means are responsive to the first analog signal for generating, for each of the blood pressure pulses, a difference measurement indicative of the difference between a peak amplitude of a pulse and an integral of the pulse. The circuit means generates signals indicating values of the systolic and diastolic pressures based on the difference measurement.

The circuit means generates the signals indicating a value of the systolic pressure substantially near the time of occurrence of a pulse having a difference measurement indicating that the static cuff pressure occurring near the time of occurrence of the pulse substantially corresponds to the systolic pressure. Correspondingly, the circuit means also generates the signals indicating a value of the diastolic pressure substantially near the time of occurrence of a blood pressure pulse having a difference measurement indicating that the static cuff pressure occurring near the time of occurrence of the pulse substantially corresponds to the diastolic pressure. The circuit means generates the signals indicating a value of systolic pressure prior to the time of occurrence of the diastolic pressure. In addition, the circuit means is further responsive to the analog signals for generating signals indicating the value of mean arterial pressure.

The circuit means comprises means for periodically sampling the analog signals in the absence of the occurrence of a blood pressure pulse. The circuit means also generates the signals indicating values of the static cuff pressure. The circuit means includes means for detecting the occurrence of a blood pressure pulse having an amplitude greater than a reference threshold value. The circuit means generates the signals indicating the values of systolic and diastolic pressures based on magnitudes of difference measurements of blood pressure pulses, relative to magnitudes of difference measurements of immediately previously occurring blood pressure pulses. Further, the circuit means generates the signals indicating a value for the systolic pressure on the basis of identification of the occurrence of a valid group of blood pressure pulses, when a predetermined number of successive difference measurements increase in amplitude. Correspondingly, the circuit means generates the signals indicating a value for the diastolic pressure on the basis of an identification of the occurrence of a valid group of pulses, when a predetermined number of successive difference measurements decrease in magnitude.

The circuit means includes pulse detection means responsive to the first analog signal for generating a pulse detection signal indicative of the occurrence of a pulse. In addition, the circuit means also includes peak detection means responsive to the first analog signal for generating, for each pulse, a peak detection signal indicative of a peak amplitude of each pulse. Still further, the circuit means includes pulse integration means responsive to the first analog signal for generating, for each of the pulses, a pulse integral signal indicative of an integral of each pulse.

Differencing means are responsive to the peak amplitude signal and to the pulse integral signal for generating, for each pulse detected by the pulse detection means, the difference measurement, with the difference measurement representing a value of the peak amplitude signal subtracted from the value of the pulse integral signal. The circuit means also includes analog-to-digital conversion means for converting the peak amplitude signal into a digital peak amplitude signal, and for converting the pulse integral signal into a digital pulse integral signal. The circuit means further includes means for periodically sampling the analog signals, in the absence of the occurrence of a blood pressure pulse, and for storing a signal representative of the most recent sample of the analog signals occurring prior to the time of the occurrence of a pulse.

In accordance with another aspect of the invention, the circuit means includes first filter means responsive to the analog pressure signals for filtering the first analog signal and for generating only the second analog signal representative of the static cuff pressure. The circuit means includes a differencing circuit responsive to the analog pressure signals for subtracting the second analog signal from the analog pressure signals, and for generating only the first analog signal. In addition, the blood pressure device includes a display means responsive to the signals indicating values of systolic and diastolic pressures, so as to provide a visual display of the systolic pressure and the diastolic pressure.

In accordance with another aspect of the invention, the blood pressure device includes pump means for applying an occluding pressure greater than the systolic pressure in the vicinity of an artery of the subject. Bleed means are provided which are adapted to be coupled to the cuff for decreasing the pressure to a pressure below the diastolic pressure. First filter means are responsive to the analog pressure signal for filtering the pressure signal and for generating only the second analog signal. Differencing circuit means are responsive to the analog signal and the second analog signal for generating an output signal comprising the first analog signal superimposed on a DC level signal. Second filter means are provided which are responsive to the output signal from the differencing circuit for removing the DC component and for generating only the first analog signal. Further, reference threshold means are provided for generating a reference threshold signal. Pulse detector means are responsive to the first analog signal and the reference threshold signal for generating a pulse detection signal having a first state when the first analog signal is greater than the reference threshold signal, and a second state when the first analog signal is less than the reference threshold signal.

In addition, reset control means are provided which are responsive to the pulse detector means for generating a reset signal, depending on the state of the pulse detector signal. Integrator means responsive to the first analog signal and to the reset signal integrate the first analog signal during the occurrence of a pulse. Peak detector means are responsive to the first analog signal and to the reset signal for generating a peak amplitude signal indicative of the peak amplitude occurring during a pulse. Processing means are provided which are responsive to the pulse detector signal for generating control signals. Sampling means are responsive to the peak detector signal, the integrator signal, the analog signal and the control signals for selectively generating digital representations of the peak amplitude signal, the integrator signal and the second analog signal. The processing means is responsive to the digital representations of the peak detector signal, the integrator signal and the second analog signal for generating, for each blood pressure pulse, a difference measurement indicative of the difference between a peak amplitude of a pulse and the integral of the pulse. The processing means generates signals indicating values of the systolic pressure and the diastolic pressure based on the difference measurements.

In accordance with another aspect of the invention, an oscillometric device includes means to detect the occurrence of pulses in an analog electrical signal, means for generating pulse characteristic signals representative of predetermined characteristics of the pulses, and means for analyzing characteristics of the pulses and for generating indicating signals on the basis of the analysis of the pulse characteristics. The improvement in accordance with the invention includes filter means responsive to the analog signal for filtering the analog signal and for generating a filtered analog signal representative only of the pulses. The pulse characteristic generating means is responsive to the filtered analog signal for generating analog pulse characteristic signals representative of predetermined characteristics of each of the pulses. The pulse characteristic signals each have a steady state value substantially at the time of occurrence of the end of a pulse.

The analyzing means includes means responsive to the detection means detecting the end of a pulse for sampling, only once for each detected pulse, each of the pulse characteristic signals, and for generating the indicating signals on the basis of an analysis of the sampled pulse characteristic signals. In this manner, the indicating signals can be generated without requiring any periodic sampling of the pulse characteristic signals or the filtered analog signal during the occurrence of pulses.

In accordance with another aspect of the invention, the invention includes a method adapted for use with an oscillometric blood pressure device for measuring systolic and diastolic pressures. The method includes the steps of applying to a cuff attachable to a test subject an occluding pressure greater than the systolic pressure in the vicinity of an artery of the subject. Also provided is the step of gradually decreasing the occluding pressure.

Analog pressure signals are generated which are representative of instantaneous cuff pressure, with the analog pressure signals including a first analog signal representative of blood pressure pulses occurring in the artery, and a second analog signal representative of static cuff pressure. For each of the blood pressure pulses, and in response to the first analog signal, a difference measurement is generated which is indicative of the difference between a peak amplitude of a pulse and an integral of the pulse. Signals are generated which indicate values of the systolic pressure and diastolic pressure based on the difference measurements.

BRIEF DESCRIPTION OF THE DRAWINGS

The invention will now be described with respect to the drawings, in which.

DESCRIPTION OF THE PREFERRED EMBODIMENT

The principles of the invention are disclosed, by way of example, in an oscillometric blood pressure measuring device 200 as depicted in FIGS. 2-9. Blood pressure measuring devices of the oscillometric type can be utilized, as previously described, for purposes of generating electrical signals representative of pulsatile pressures, and for analyzing these signals so as to determine systolic, mean and diastolic blood pressures. The blood pressure measuring device 200 overcomes or minimizes several of the previously-described problems of known blood pressure measuring devices employing oscillometric techniques and utilized in a manner as previously described in the section entitled "Background Art."

The oscillometric blood pressure measuring device 200 is particularly advantageous in that it will determine systolic and diastolic blood pressures on a "real time" basis, in contrast to oscillometric blood pressure measuring systems requiring storage of substantial amounts of data and "batch" processing of this data following a pressure deflation cycle so as to determine systolic and diastolic blood pressures. In addition, and in accordance with the invention, this real time processing is provided in part by the use of analog circuitry, and without requiring any relatively rapid sampling of signals representative of pressures, at a rate substantially exceeding an expected heart rate.

Figure 2:
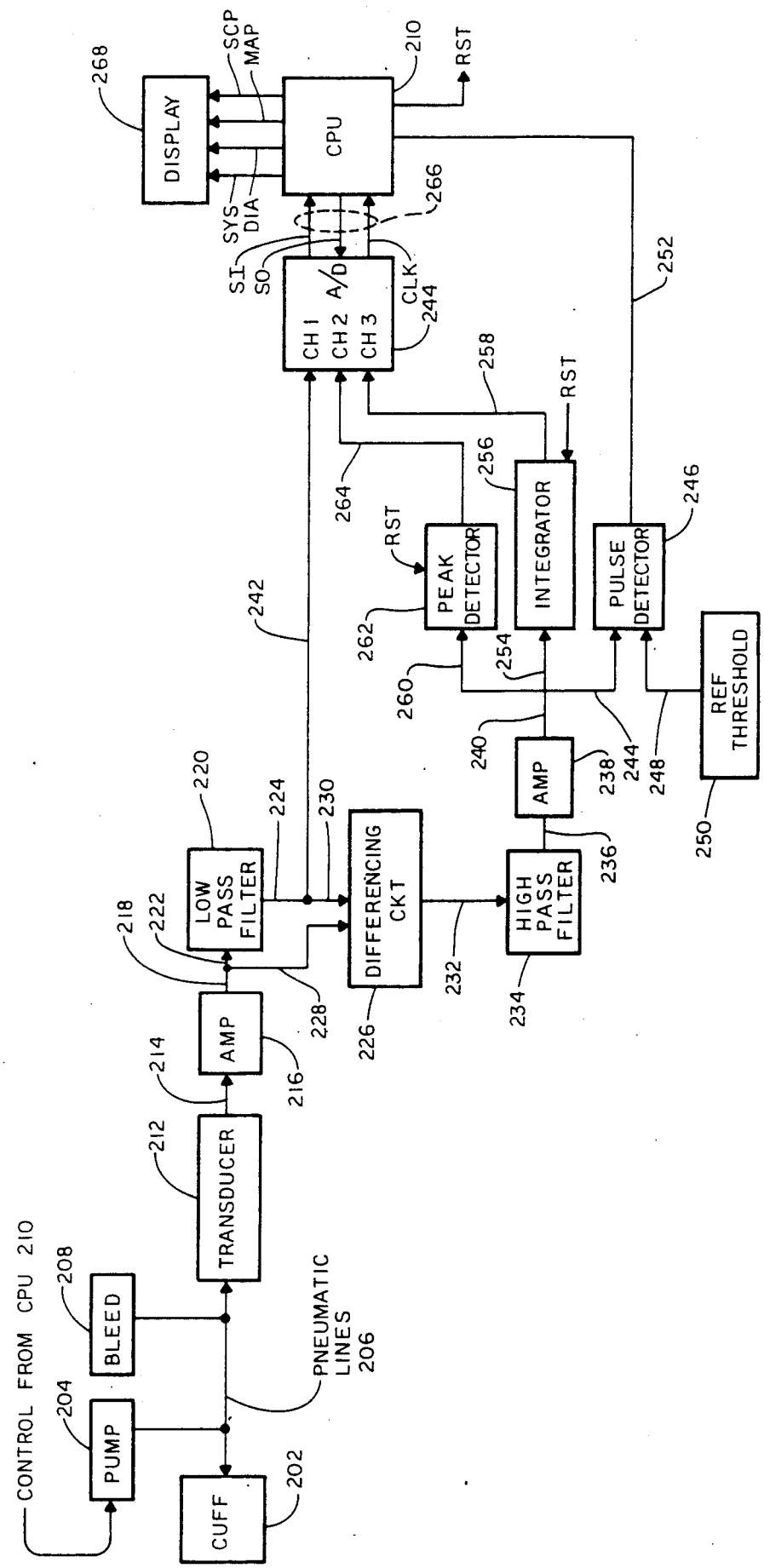
FIG. 2 is a block diagram of an oscillometric blood pressure measuring device in accordance with the invention.

The oscillometric blood pressure measuring device 200 is illustrated in a relatively simplified block diagram format in FIG. 2. As shown in FIG. 2, the blood pressure measuring device 200 comprises an occluding pneumatic cuff 202 which may be relatively conventional in design, and is typically adapted to be fitted around the upper arm of a test subject (not shown) for occluding an artery, such as the brachial artery therein. While the arm is most conveniently utilized, other body members (e.g. the thigh) may also be used.

As will be explained in greater detail herein, the measuring device 200 can include a motor/pump 204 which is connected to the cuff 202 through a pneumatic line 206. The motor/pump 204 can be conventional in design and is utilized to automatically inflate the pneumatic cuff 202 for purposes of applying pressure sufficient to occlude the artery under test. Correspondingly, the measuring device 200 can also include a bleed device 208 which can comprise conventional valve arrangements and is also connected to the cuff 202 through pneumatic line 206. The bleed device 208 is employed to bleed air from the cuff 202 for purposes of deflating the cuff 202. The motor/pump 204 and bleed device 208 can be operated through control signals applied from central processing unit (CPU) 210. Any of several different types of automated motor/pump and bleed device arrangements can be employed with a measuring device in accordance with the invention. Further, although it would not be preferable, it would be possible to utilize manually-operated pump devices (such as a conventional pump-up inflation bulb and the like) and bleed valve arrangements without departing from the novel concepts of measuring devices in accordance with the invention.

As further illustrated in FIG. 2, the cuff 202 is connected to a pressure transducer 212 through the pneumatic line 206. The transducer 212 is conventional in structure and function, and generates an analog signal as an output signal on line 214 which is representative of both static cuff pressure and pulsatile changes in cuff pressure caused by pressure changes in the arterial system, and specifically in the particular artery to which the cuff 202 is applied. As previously described, such pulsatile changes in cuff pressure (referred to herein as pulsatile signals or pulsatile cuff pressure signals) can result not only from true changes in arterial blood pressure, but can also result from unwanted "artifacts", such as pulses resulting from movements of the test subject's arm.

The analog signal generated by the transducer 212 on line 214 is applied as an input signal to a conventional first amplifier 216 as further illustrated in FIG. 2. The amplifier 216 can be conventional in structure and generates an amplified analog signal representative of both static cuff pressure and pulsatile changes in cuff pressure, and applies the amplified signal as an output signal on line 218. As further shown in FIG. 2, the amplified signal on line 218 is applied as an input signal to a low pass filter 220 via line 222. As previously described, the analog signal on line 222 represents both static cuff pressure and pulsatile changes in cuff pressure. The low pass filter 220 operates to provide a means for filtering high frequency transients, similar undesired signals and other signals above the low frequency band. The low pass filter 220 therefore removes the portion of the analog signal on line 222 representative of pulsatile changes in cuff pressure. Accordingly, the signal generated by low pass filter 220, which is applied as an output signal on line 224, is an analog signal substantially representative of only the static cuff pressure as detected by the pressure transducer 212.

Along with the application of the analog signal on line 218 as an input signal to the low pass filter 220, the analog signal on line 218 is also applied directly as an input signal to a comparator or "differencing" circuit 226 via line 228. More specifically, the analog signal on line 228 will be applied as an input signal to the "+" input terminal of the differencing signal 226. Simultaneously, the output signal to the low pass filter 220 on line 224, representative only of static cuff pressure, is applied on line 230 as an input signal to the "−" terminal of the differencing circuit 226. Again, the analog signal output from the low pass filter 220 on lines 224 and 230 can be characterized as comprising a first analog signal portion representative of the static cuff pressure. Correspondingly, the analog signal on line 228 can be characterized as comprising not only the first analog signal portion representative of the static cuff pressure, but also comprising a second analog signal portion representative of the pulsatile changes in cuff pressure. The differencing circuit 226 operates to subtract the analog signal on line 230 from the analog signal on line 228. Accordingly, the output of the differencing circuit 226, applied as a signal on line 232, substantially corresponds to a removal of the first analog signal portion (representative of static cuff pressure) from the signals representative of first and second analog signal portions. Therefore, the analog signal on line 232 essentially represents only the second analog signal portion, i.e. the portion representative of the pulsatile changes in cuff pressure. The analog signal on line 232 is applied as an input signal to a conventional high pass filter circuit 234. Although the analog signal on line 232 comprises the second analog signal portion representative of pulsatile changes in cuff pressure, this signal will also have a DC component as a result of the conventional operation of the differencing circuit 226. The high pass filter circuit 234 operates to essentially "strip" the DC component from the analog signal on line 232. The output of the high pass filter circuit 234 is applied as an output signal on line 236. In accordance with the foregoing, the signal on line 236 is representative only of pulsatile changes in cuff pressure, with no DC bias level associated therewith.

After removing the DC component from the second analog signal portion representative of cuff pressure pulsatile changes, the analog signal on line 236 is applied as an input signal to a conventional amplifier 238. Amplifier 238 operates to linearly amplify the second analog signal portion for purposes of increasing the signal gain for subsequent processing. The output of the amplifier 238 is applied as an output signal on line 240. In accordance with all of the foregoing, the analog signal on line 240 can be characterized as a second analog signal portion representative only of the cuff pressure pulsatile changes.

As earlier described, the output signal from the low pass filter circuit 220 on lines 224 and 230 can be characterized as comprising a first analog signal portion representative only of static cuff pressure. This signal is further applied to line 242 and operates as an input signal to the analog/digital (A/D) circuit 244 which will be described in subsequent paragraphs herein. However, with reference to FIG. 2, the analog signals on lines 240 and 242 therefore represent second and first analog signal portions, respectively, with the signal on line 240 representative only of pulsatile changes in cuff pressure, and the signal on line 242 representative of corresponding static cuff pressure.

The analog signal on line 240, comprising the second analog signal portion representative only of pulsatile changes in cuff pressure, is applied as an input signal to several analog function devices for purposes of generating signals indicating the occurrence of a pulse, and representative of certain characteristics of each pulse. As described in subsequent paragraphs herein, these pulse characteristics are utilized for determining blood pressure parameters, including systolic and diastolic pressures, and mean arterial pressure (conventionally referred to as "MAP"). In accordance with the invention, these characteristics are selected so as to accurately distinguish between true pulses and artifacts resulting from other than heart beats.

Specifically, and with further reference to FIG. 2, the second analog signal portion on line 240 is applied as an input signal on line 244 to a pulse detector circuit 246. Also applied as an input signal to the pulse detector circuit 246 is a reference threshold signal on line 248 which is generated from a conventional reference threshold circuit 250. For purposes of detecting the occurrence of pulsatile changes in cuff pressure, the pulse detector circuit 246 is adapted to generate, as an output signal, a pulse detection signal on line 252 during any time period when the second analog signal portion on line 244 is greater than the reference threshold signal on line 248. Signal amplitudes of the second analog signal portion on line 244 which do not rise above the reference threshold signal on line 248 are assumed to be noise signals or the like, and are not considered to be indicative of the occurrence of a pulse. Although the concept of employing a reference threshold signal for determining the existence or absence of a pulse comprises one particular type of design, it is apparent that numerous other circuit designs could be employed for purposes of determining the occurrence of a pulse. Accordingly, the particular types of circuit arrangements employed with the pulse detector circuit 246 and reference threshold circuit 250 do not embody any of the principal concepts of a blood pressure monitoring device in accordance with the invention.

Unlike the analog signals previously described herein with respect to the circuitry illustrated in FIG. 2, the signal output of the pulse detector circuit 246 on line 252, representative of the existence or absence of a pulse, can be characterized as a binary signal in that it can include only two states. One of the states will be indicative of the absence of a pulse, while the other state will be indicative of the occurrence of a pulse. The signal output of the pulse detector circuit 246 on line 252 is applied as an input signal to the CPU 210. As described in subsequent paragraphs herein, this signal is utilized with other input signals by the CPU 210 for purposes of determining the blood pressure parameters.

In addition to the second analog signal portion on line 240 being applied as an input signal to the pulse detector circuit 246, the signal on line 240 is also applied as an input signal on line 254 to an integrator circuit 256. The integrator circuit 256 is adapted to integrate the signal input on line 254, and apply the integrated output signal on line 258. For each pulse, the integrator output signal on line 258 is essentially representative of the total "energy" of the pulse. In mathematical terms, the integrator output signal represents the total "area" under the pulse, if the pulse amplitude is illustrated in two dimensions as a function of time.

For purposes of generating an integrator output signal on line 258 representative of a "true" integral of each pulsatile change in cuff pressure, the integration circuit 256 must be "reset" to an initial state prior to the start of each pulse. Otherwise, as a result of the integration of prior pulses, and as a result of the occurrence of any noise or other spurious signals which may occur on line 254, the integration circuit 256 would not provide a true representation of each pulse integral. Accordingly, a reset signal RST is applied as an input signal to the integrator circuit 256. The reset signal RST can be of various embodiments. For example, reset signal RST can be a twostate, wherein in one first state the circuit 256 is "allowed" to integrate. In the other second state, integration would be inhibited. Accordingly, the signal RST would be maintained in the second state except during the occurrence of a pulse. The reset signal RST, in the particular embodiment in accordance with the invention as illustrated in FIG. 2, is generated as an output signal from the CPU 210. A more detailed description of the functional operation of the reset signal RST and the CPU 210 will be set forth in subsequent paragraphs herein.

Referring again to FIG. 2, the second analog signal portion on line 240 is further applied on line 260 as an input signal to a peak detector circuit 262. The peak detector circuit 262 is adapted to generate an output signal on line 264 corresponding to the peak amplitude of each pulsatile pressure signal detected by the pulse detector circuit 246. Accordingly, at the end of the occurrence of a pulsatile pressure signal (or at any time following the occurrence of the maximum amplitude of the pulsatile pressure signal), the output signal of peak detector circuit 262 on line 264 is essentially a steady state signal representing the maximum amplitude achieved during the occurrence of the corresponding pulse. As with the integrator circuit 256, a reset signal RST is also applied as an input signal to the peak detector circuit 262. This reset signal, again being applied from the CPU 210, is required for purposes of inhibiting the peak detector circuit 262 in the absence of a pulse, and enabling circuit 262 during the occurrence of a pulse.

In accordance with the foregoing, for each pulsatile pressure signal occurring on line 240, several signals are generated, indicating the occurrence of the pulse and representative of certain pulse characteristics. Specifically, the existence of a pulsatile pressure signal is indicated by the output signal of the pulse detector circuit 246 on line 252. Correspondingly, the integral of each pulse is obtained from the integrator circuit 256 and is represented by the signal on line 258. Further, the maximum or peak amplitude of each pulse is obtained by the peak detector circuit 262 and represented by the signal on line 264.

Continuing to refer to FIG. 2, the oscillometric blood pressure measuring device 200 includes a relatively convention analog/digital (A/D) circuit 244. The A/D circuit 244 includes a series of input channels, comprising channels 1, 2 and 3 (identified in FIG. 2 as CH1, CH2, and CH3, respectively). In the particular embodiment show in FIG. 2, the A/D converter 244 also includes a "symbolic" output line 266. The symbolic output line 266 actually comprises three signal lines, identified in FIG. 2 as lines SI, SO and CLK. The three signal lines SI, SO and CLK are interconnected between the A/D converter 244 and the CPU 210.

As described subsequently herein, in response to input "instruction"" signals from CPU 210, the A/D converter circuit 244 operates to convert analog input signals on a selected one of the channels CH1, CH2 or CH3 to digital signals which are generated, in serial format, as binary output data signals on line SI. These binary output data signals are further applied as input signals to CPU 210 from line SI.

In accordance with the foregoing, the A/D converter circuit 244, unlike many other types of A/D converters providing parallel digital output data, is a serial output device. That is, the output data generated on line SI are in the form of serial binary pulses. In the particular embodiment illustrated in FIG. 2, the A/D converter circuit 244 is responsive to serially applied periodic clock pulses applied as input signals from the CLK line. Correspondingly, binary signals in the form of an "instruction" code are serially applied as input signals from line SO. These binary instruction signals, decoded by the A/D converter circuit 244 in accordance with the clock pulses from line CLK, provide the A/D converter 244 with data indicative of the particular one of the channels CH1, CH2 or CH3 selected for analog/digital conversion. The particular instruction code applied as an input on line SO can also include other data, such as an indication of when the generation of digital output data signals on line SI are to commence. Both input data signals on line SO and output data signals on line SI will essentially be "strobed" in accordance with the periodic clock pulses appearing on line CLK. For example, a binary input pulse or a binary output pulse may be characterized as occurring substantially simultaneously with each positive transition of a clock pulse on line CLK.

Although the foregoing describes a particular embodiment of the A/D converter circuit 244, with respect to intercommunication with CPU 210, it should be emphasized that various other types of circuit communication arrangements may be employed. Further, circuitry in accordance with the invention need not be limited to the use of serial data transmission. Various other types of circuit arrangements can be employed without departing from the spirit and scope of the principal concepts of the invention.

As described in greater detail subsequently herein, the CPU 210 operates to perform various functions associated with the oscillometric blood pressure measuring device 200. In particular, the CPU 210 will be responsive to signals on line 252 representative of the occurrence of a pulsatile change in cuff pressure. Accordingly, the output signal from the pulse detector circuit 246 is applied as an input signal to the CPU 210 from line 252. In response to a signal indicating the occurrence of a pulse, the CPU 210 will operate to apply appropriate output signals on line CLK and line SO so as to obtain data representing certain characteristics of the pulse, along with data representative of a static cuff pressure substantially corresponding to the occurrence of a pulse. As shown in FIG. 2, the pulse characteristics obtained by the CPU 210 through the A/D converter circuit 244 will include the integral of the pulse (applied as an input to channel CH3 of the converter circuit 244) and the peak amplitude of the pulse (applied as an input signal to channel CH2 from the peak detector circuit 262). In addition, a static cuff pressure which may be characterized as substantially corresponding to the occurrence of the pulse is obtained from the input signal on line 242 applied to channel CH1 of the A/D converter circuit 244. Data representative of these pulse characteristics and the static cuff pressure are generated as output data from the A/D converter circuit 244 on line SI, and applied as input data to the CPU 210. In this regard, the A/D converter circuit 244, with the capability of generating output data from a selected one of the input channels CH1, CH2 or CH3, can be characterized as operating in part as a multiplexer1 circuit for purposes of sequentially applying output data on line SI. However, the generation of this output data on line SI is controlled in part by the input clock pulses from line CLK and the instruction code applied as input signals on line SO from the CPU 210.

The CPU 210 will operate so as to perform certain analyses of the characteristics of each detected pulse. These analyses are utilized for purposes of determining systolic and diastolic blood pressures, along with the mean arterial pressure. When the CPU 210 has made a determination of the systolic pressure, appropriate output signals representative of the systolic pressure can be generated on line SYS as further illustrated in FIG. 2. The output signals representative of systolic pressure can be applied as input signals to a conventional display device 268. The display device 268 can be any of numerous types of convention visual display devices, such as LCD's and alike.

When the CPU 210 has determined, by analyses of the pulse characteristics, the occurrence of the diastolic pressure, output data can be applied as signals on line DIA. This output data on line DIA can be applied as input data to the display device 268. Correspondingly, when the CPU 210 has determined the occurrence of mean arterial pressure, appropriate output data representative of this pressure can be generated on line MAP. In addition to the foregoing, if it is desired to maintain a "running" display of static cuff pressure as the pressure in the cuff 202 is deflated, the CPU 210 can operate so as to generate appropriate output data representative of the static cuff pressure on line SCP. The output data signals on lines SYS, DIA, MAP and SCP can all be applied as input signals to the display device 268 for purposes of providing an appropriate visual display to the user.

As will be described in greater detail herein, and as will be apparent from the description of the operation of the CPU 210, the oscillometric blood pressure measuring device 200 can operate in a "real time" mode. That is, a number of known blood pressure measuring devices employing oscillometric techniques are required to periodically obtain samples of all pulses occurring throughout the cuff pressure deflation cycle, prior to performing any pulse analyses or computations of data so as to determine parameters such as systolic and diastolic blood pressures. In contrast, and in accordance with the invention, the oscillometric blood pressure measuring device 200 operates in a real time mode in that the pulse characteristics are analyzed in a manner so as to determine systolic pressure substantially at or near the actual time of occurrence of systole. Correspondingly, at such time, the CPU 210 will operate so as to substantially immediately generate output data and apply the same to line SYS for purposes of displaying systolic pressure on the visual display device 268. Correspondingly, diastolic pressure is also determined substantially at its time of occurrence, with appropriate data applied on line DIA to the display device 268. In this manner, there is no requirement for essentially "post-processing" data following the entirety of a pressure deflation cycle, before analyzing pulse characteristics and computing blood pressure parameters.

Figure 3:
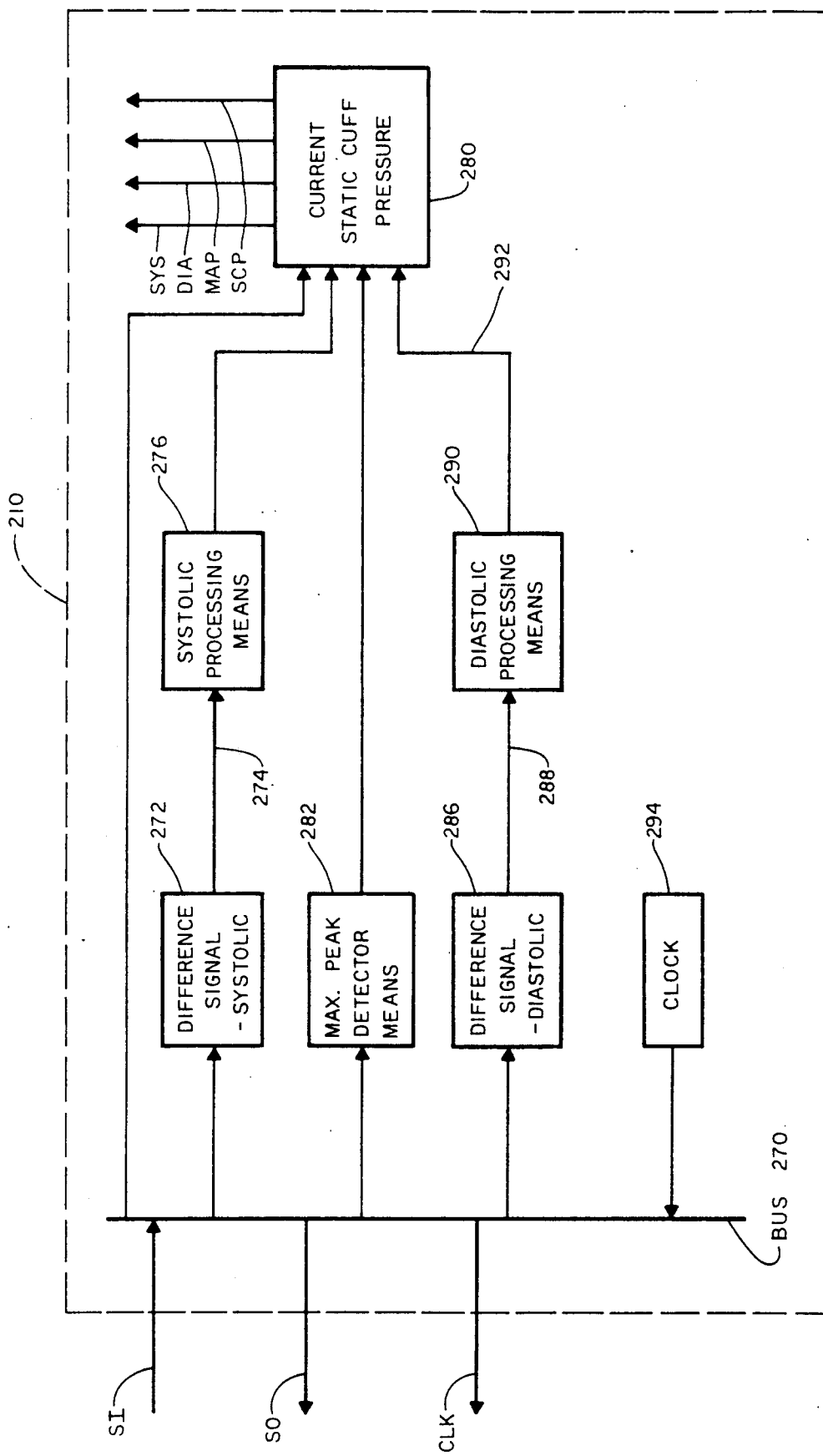
FIG. 3 is a representative diagram of certain functions which may be performed within the central processing unit (CPU) for an oscillometric blood pressure measuring device in accordance with the invention.

FIG. 3 illustrates a purely "symbolic" representation of certain of the functions performed by the CPU 210 in accordance with the invention. It should be emphasized that the particular embodiment of an oscillometric blood pressure measuring device 200 in accordance with the invention as described herein represents only one particular embodiment of various circuit configurations which may be employed without departing from the spirit and scope of the novel concepts of the invention. For example, as described in subsequent paragraphs herein, many of the functions associated with the blood pressure measuring device 200 are performed by software processes in CPU 210. However, many of these processes could also be performed by the use of discrete circuitry.

To illustrate certain of the functions performed by CPU 210, FIG. 3 shows a symbolic bus 270 to which data signals from the A/D converter circuit 244 are applied on line SI. In accordance with the invention, data signals from line SI and the bus 270 corresponding to the peak amplitude of each pulsatile pressure signal and the signals corresponding to the integral of each pulsatile pressure signal are applied to a difference signal means 272. The difference signal means 272 operates to essentially subtract the digital representation of the peak amplitude of the pulsatile pressure signal from the digital representation of the integral of the pulsatile pressure signal. The output of the difference signal means 272, symbolically represented as being applied on line 274, is utilized by a systolic processing means 276. The systolic processing means 276 is responsive to the difference signal on line 274 for purposes of determining whether the difference signal value for this particular pulse, with reference to the value of the difference signal associated with the previous pulse, corresponds to the occurrence of systole. If such a determination is made, the systolic processing means 276 can transmit appropriate indication signals on symbolic line 278 to the static cuff pressure latch means 280. The static cuff pressure latch means essentially obtains the "most recent" value of static cuff pressure obtained on line SI from the A/D converter circuit 244. The latch means 280 can be considered functionally responsive to the indication signals on line 278 so as to transmit appropriate data signals on line SYS for display of the static cuff pressure on the visual display 268.

The systolic processing means 276 essentially comprises a functional analysis of the difference signal computed for the present pulse, relative to different signals computed for prior pulses. As an example of a particular functional process which may be utilized to determine the occurrence of systolic pressure, and as described in subsequent paragraphs herein, systolic pressure may be assumed to be equivalent to the static cuff pressure substantially associated with the current pulse, if a predetermined number of successive difference signals (associated with a predetermined number of successive pulses) have continually increased in magnitude. In such event, a "valid" pulse group can be assumed to have occurred, and the systolic pressure can be considered as the most recent determination of static cuff pressure at the time of the occurrence of the current pulse.

For purpose of determining mean arterial pressure, the data signals received on line SI from A/D converter circuit 244 which represent the peak amplitude for the current pulse, are applied from the bus 270 as input signals to a maximum peak detector means 282. The maximum peak detector means 282 is a functional representation of the process of determining the occurrence of the particular pulsatile pressure signal having the highest amplitude. In accordance with conventional blood pressure measuring devices, the static cuff pressure associated with the occurrence of the pulse of maximum amplitude is characterized as the mean arterial pressure. Accordingly, when the maximum peak detector means 282 determines this maximum peak amplitude pulsatile pressure signal, an appropriate indication signal can be applied on symbolic line 284 as an input signal to the static cuff pressure latch means 280. In response, the static cuff pressure latch means 280 can apply output data signals on line MAP which, in turn, are applied as input signals to the display device 268 for purposes of displaying the mean arterial pressure.

Correspondingly, after systolic blood pressure has been determined, signals on line SI representative of the integral of the current pulse and the peak amplitude of the current pulse can be applied as input signals to a second difference signal means 286. In a manner similar to the first difference signal means 272, the second signal detector means 286 functions so as to generate a difference signal representative of the digital representation of the peak amplitude of the current pulse subtracted from the integral of the current pulse. This difference signal is applied on symbolic line 288 as an input signal to a diastolic processing means 290. The diastolic processing means 290 is a functional representation of a particular process operating on the difference signal associated with the current pulse, for purposes of determining whether the current pulse essentially represents the occurrence of diastolic pressure.

As an example of a particular process which may be employed for this determination, and in a manner similar to the process which may be employed for determining systolic pressure, the diastolic determination process may determine when a pulse "group" has occurred, wherein each successive difference signal associated with successive pulses has decreased in magnitude for each of a predetermined number of successive pulses. In such event, a valid pulse group may be assumed to have occurred, and the diastolic pressure may be assumed to be the most recent static cuff pressure obtained substantially at the time of occurrence of the current pulse. When such a determination is made, appropriate indication signals can be applied on symbolic line 292 as input signals to the static cuff pressure latch means 280. In response to such indication signals from the diastolic processing means 290, the static cuff pressure latch means 280 can apply data signals representative of the current static cuff pressure as output signals on line DIA.

Also in accordance with circuitry illustrated in FIG. 3, the static cuff pressure latch means 280 can include an output line SCP on which current static cuff pressures obtained from the A/D converter circuit 244 through line SI can be applied to the visual display device 268. Finally, for purposes of symbolic representation, FIG. 3 also illustrates a clock circuit 294 operative for purposes of applying clock signals to bus 270 and further to line CLK as input clock signals to the A/D converter circuit 244. Again, the representations shown in FIG. 3 are merely for purposes of understanding, and comprise only functional representations of processes performed by the blood pressure measuring device 200 in accordance with the invention, rather than any representation of actual circuitry or software.

As previously described, the functional operations represented in FIG. 3 can be implemented by means of the central processing unit 210. The particular structural configuration of the central processing unit 210 can comprise numerous types of processor configurations. For example, the CPU 210 can be in the form of a programmable device such as the microcomputer 210 depicted in FIG. 5. As shown therein, the microcomputer 210 comprises a conventional microprocessor 300. Although various types of well-known and commercially available devices can be employed for the microprocessor 300, one typical internal configuration of a microprocessor 300 is shown in FIG. 4, and a brief and simplistic description thereof will be provided.

Figure 4:
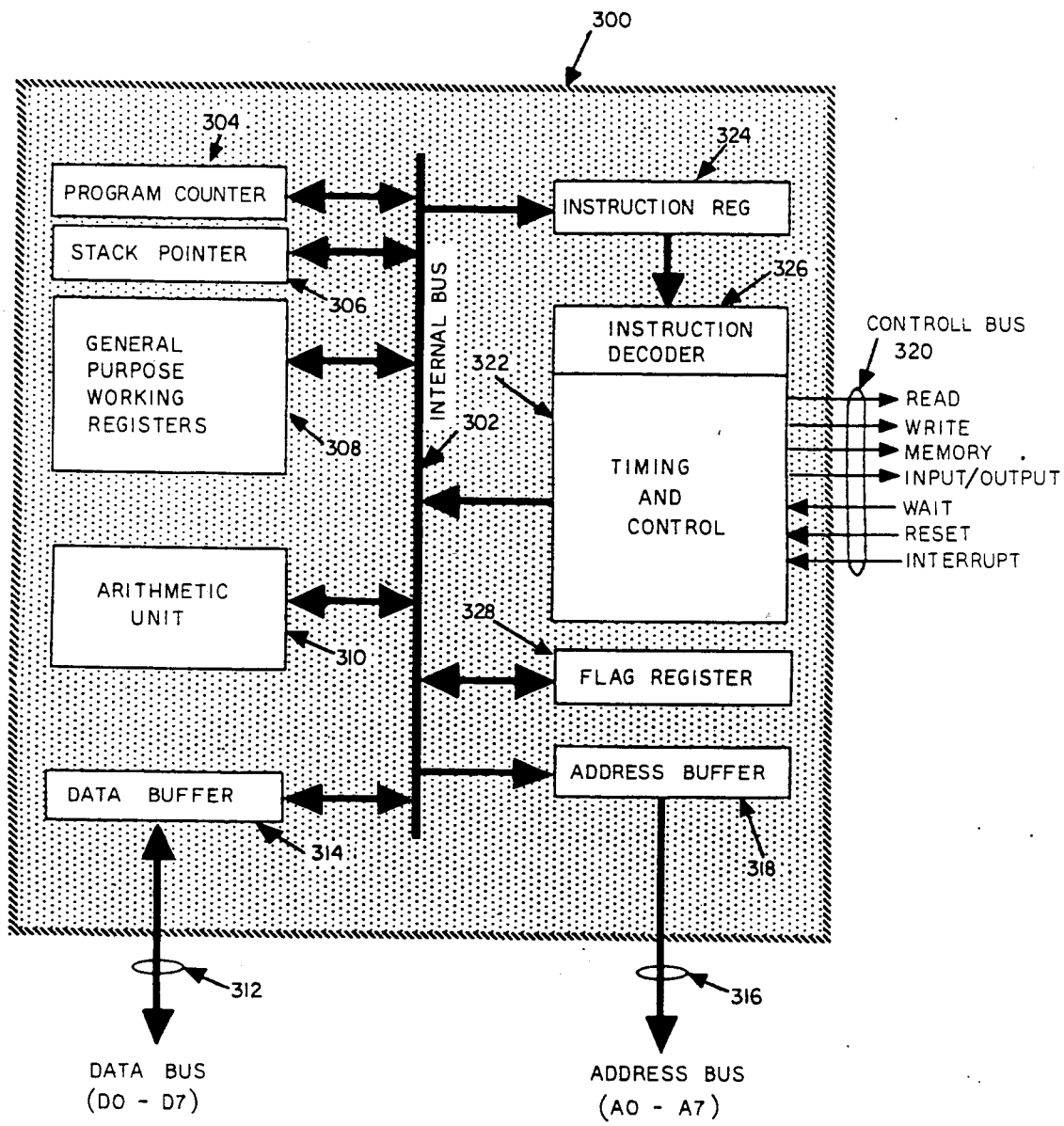
FIG. 4 is an example of a microprocessing unit.
Figure 5:
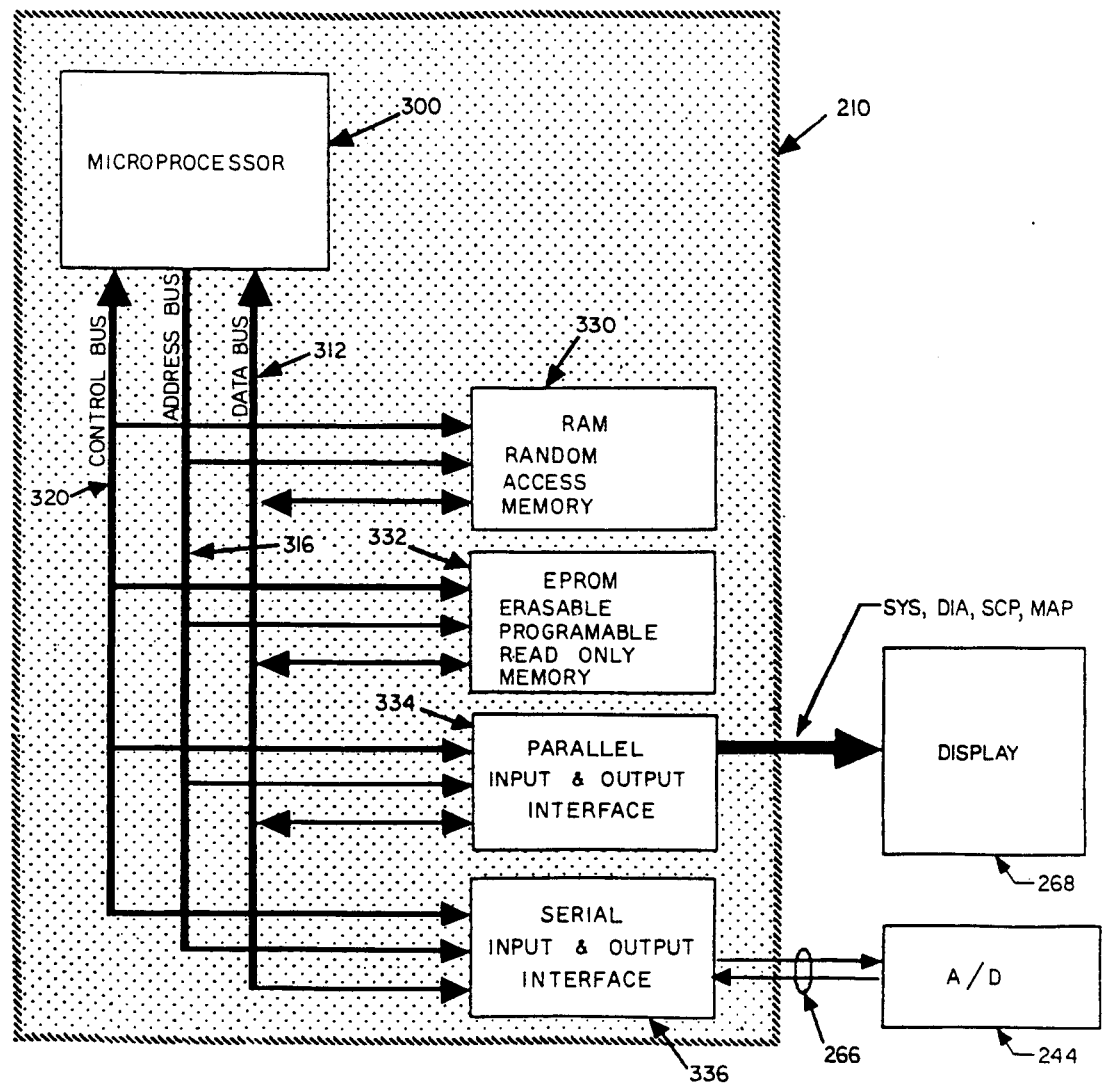
FIG. 5 is a further example of a microprocessing unit.

Referring specifically to FIG. 4, the microprocessor 300 comprises an internal bus 302 which provides a means for bidirectional communication between conventional circuit components of the microprocessor 300. For example, signals can be transmitted to and received from the program counter 304, which comprise signals representative of the "next" instruction in the microcomputer memory to be executed. Communication can also be provided between the internal bus 302 and microprocessor components such as the stack pointer 306, general purpose registers 308 and arithmetic unit 310. Each of these processor components is well known to those skilled in the art of internal computer system design.

The transmission and reception of data from memories and other components of the central processing unit 210 is provided by the data bus 312 which is connected to the internal bus 302 through a conventional data buffer 314, so as to provide bidirectional communication therewith in the form of 8-digit parallel binary signals. The internal bus 302 is also connected to an address bus 316 through an address buffer 318. The microprocessor 300 can provide, for example, 8-digit parallel binary address signals on the bus 316 for directed communication between the microprocessor 300 and the various memories and other devices having signal communications through the data bus 312.

Conventional system control is provided by interconnection of a control bus 320 to timing and control circuitry 322. Communications signals from the conventional timing and controls circuitry 322 can be applied to various components of the microprocessor 300 through the internal bus 302.

The microprocessor 300 also includes other conventional circuit components, including an instruction register 324. The instruction register 324 comprises a register to which the "next" instruction is stored for purposes of decoding and execution. The data within the instruction register 324 is applied to an instruction decoder 326 which comprises conventional circuitry for decoding the instruction data received from the next program location in memory. The microprocessor 300 can also include such conventional components as a flag register 328 utilized for various programming control within the processor 300.

The control bus 320 can be characterized as comprising a series of individual command signal leads. The signal leads include "transmitted" commands shown in FIG. 4 as the "read", "write", "memory" and "I/O" commands. In addition, the control bus 320 is adapted to apply certain "received" commands to the timing and control circuitry 322. These commands are symbolically shown in FIG. 4 as the "received", "wait", "reset" and "interrupt" commands. The use of these commands is well known in the field of computer system design. For example, if data is to be read from a certain address location in a memory of the CPU 210, "enable" signals can be applied to the "read" and "memory" command leads from the timing and control circuitry 322. Correspondingly, the address of the particular memory location to be read can be transmitted on address bus 316, while the data to be read from the particular memory location will be applied to the microprocessor 300 on data bus 312. Similarly, when data is to be applied to a particular I/O device associated with the microcomputer 210, "enable" signals can be applied on the "write" and "I/O" signal command leads from the timing and control circuitry 322. Correspondingly, the address destination of the I/O device can be applied on address bus 316, while the particular data to be transmitted to the I/O device can be applied on data bus 312. Again, the circuitry associated with microprocessor 300, and the microprocessor 300 itself, are well known in the art. Any one of numerous commercially available microprocessors can be adapted for use as the microprocessor 300.

Returning again to FIG. 5, the central processing unit 210 includes memory storage elements such as the random access memory (RAM) 330. The RAM 330 is conventional in design and includes memory locations wherein data may be stored and modified during execution of program sequences. Similarly, for storage of "permanent" data or instructions wherein modifications must be made only occasionally, a conventional erasable-programmable read only memory (EPROM) 332 is also employed.

Both the RAM memory 330 and the EPROM memory 332 are interconnected with the microprocessor 300 so as to allow control and address location signals to be applied on the control bus 320 and address bus 316, respectively. In addition, for purposes of reading data from the memories into the microprocessor 300, and for writing data into the memories, bidirectional communication is established between the RAM memory 330, EPROM memory 332 and the microprocessor 300 through data bus 312.

For purposes of intercommunication with external devices, the central processing unit 210 can also include a parallel I/O interface module 334 and a serial I/O interface module 336. The parallel interface module 334 provides a means for transmitting and receiving data signals between the microprocessor 300 and external devices which generate and receive signals in parallel format. For example, the parallel interface module 334 may be utilized as the microcomputer interface for the data signals transmitted to the display device 268 on lines SYS, DIA, MAP and SCP illustrated in FIG. 2. The interface module 334 can also be utilized for purposes of transmitting parallel data signals to other appropriate devices, such as alarms, and the like. The serial interface module 336 is utilized to interface with external devices in a serial format. For example, data signals transmitted to and received from the A/D converter circuit 244 previously described with respect to FIG. 2 will be in serial format, and will be interfaced with the microprocessor 300 through the interface module 336.

Like the RAM memory 330 and EPROM memory 332, the interface modules 334 and 336 are interconnected to the microprocessor 300 through the control bus 320 and address bus 316 for purposes of applying control and address information data signals, respectively, to each of the modules. In addition, the interface modules 334 and 336 are interconnected to the processor 300 through data bus 312 so that data signals are bidirectionally transferable between the modules 334, 336 and processor 300. It should be emphasized that the general circuitry of the microcomputer 210 and the functional operations associated therewith are well known in the field of computer system design. Accordingly, any one of numerous commercially available microcomputers can be adapted for use as microcomputer 210. In addition, it should also be emphasized that the central processing unit 210 need not specifically be of a microcomputer design. Other types of digital computers could be employed in accordance with the invention. Indeed, although it may not be a preferable embodiment of the central processing unit 210, discrete circuitry could be designed to perform the requisite functions of the unit 210.

The operation of the oscillometric blood pressure measuring device 200 will now be described with respect to FIG. 2 and FIGS. 6–9. As previously described with respect to FIG. 2, the pump 204, which may be operated under control of the CPU 210, is utilized to inflate the cuff 202 to a pressure above systolic pressure. Although not specifically described herein, various "algorithms" or other functional processes can be utilized with the measuring device 200 so as to ensure that the cuff is inflated above systolic pressure. For example, if the cuff pressure is inflated to a predetermined value, and a pulse is detected within a period of time less than a predetermined time period, the particular deflation cycle can be aborted and the cuff can again be inflated to a pressure which is a predetermined value above the initial maximum pressure. That is, in the event of a pulse occurring "too soon" after initiation of the deflation cycle, it may be assumed that there is a possibility that the cuff is not pressurized above systolic pressure. Each time that an "abort" may occur in this manner, the maximum cuff pressure can continue to be increased, up to a certain predetermined value. Various other types of functional determinations can be utilized to ensure that the initial maximum cuff pressure exceeds systolic pressure.

Figure 9:
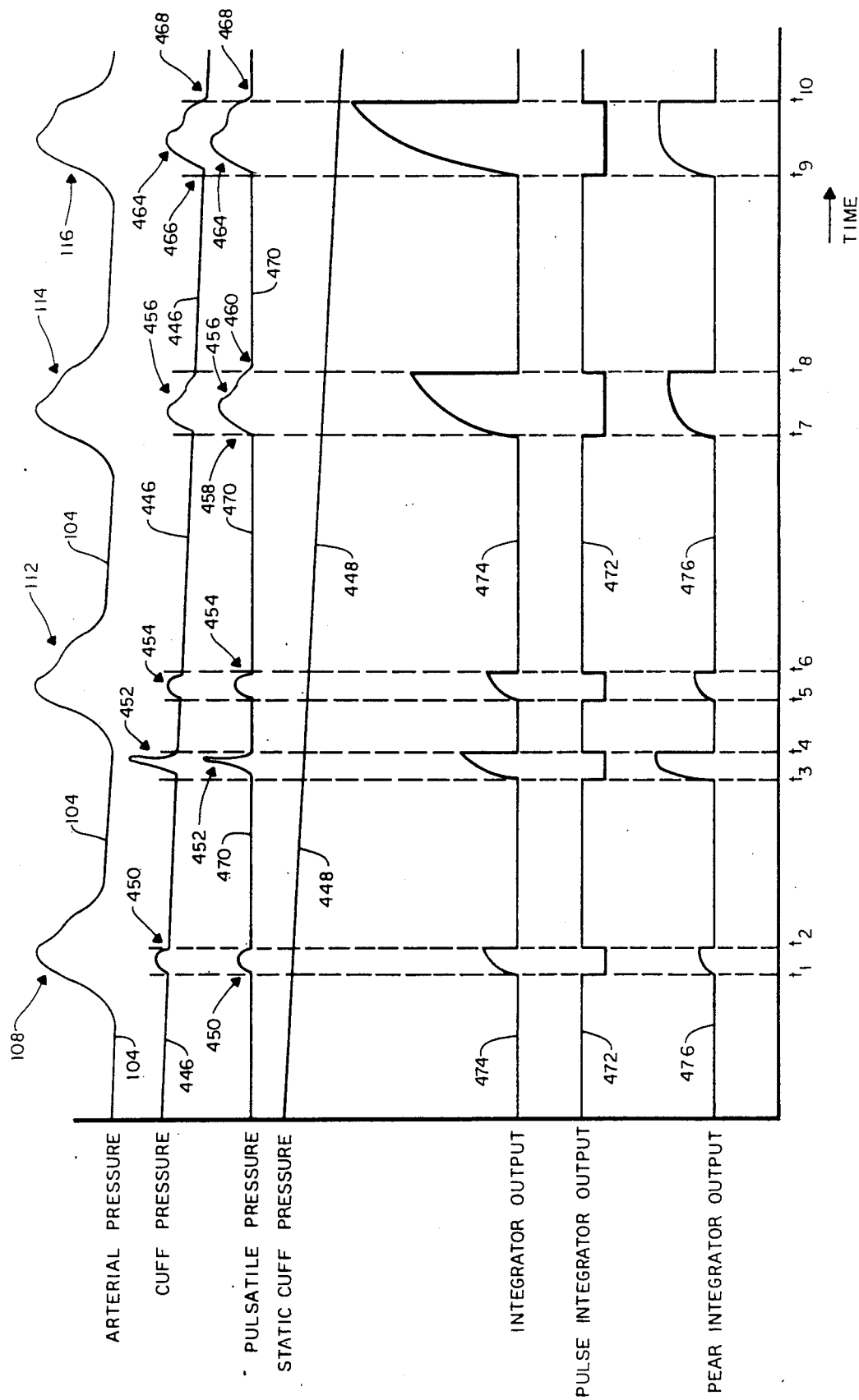
FIG. 9 shows various waveforms detected by a blood pressure measuring device in accordance with the invention as illustrated in FIG. 2, and further shows various signals and wave forms generated by components of the device shown in FIG. 2.
Figure 9:
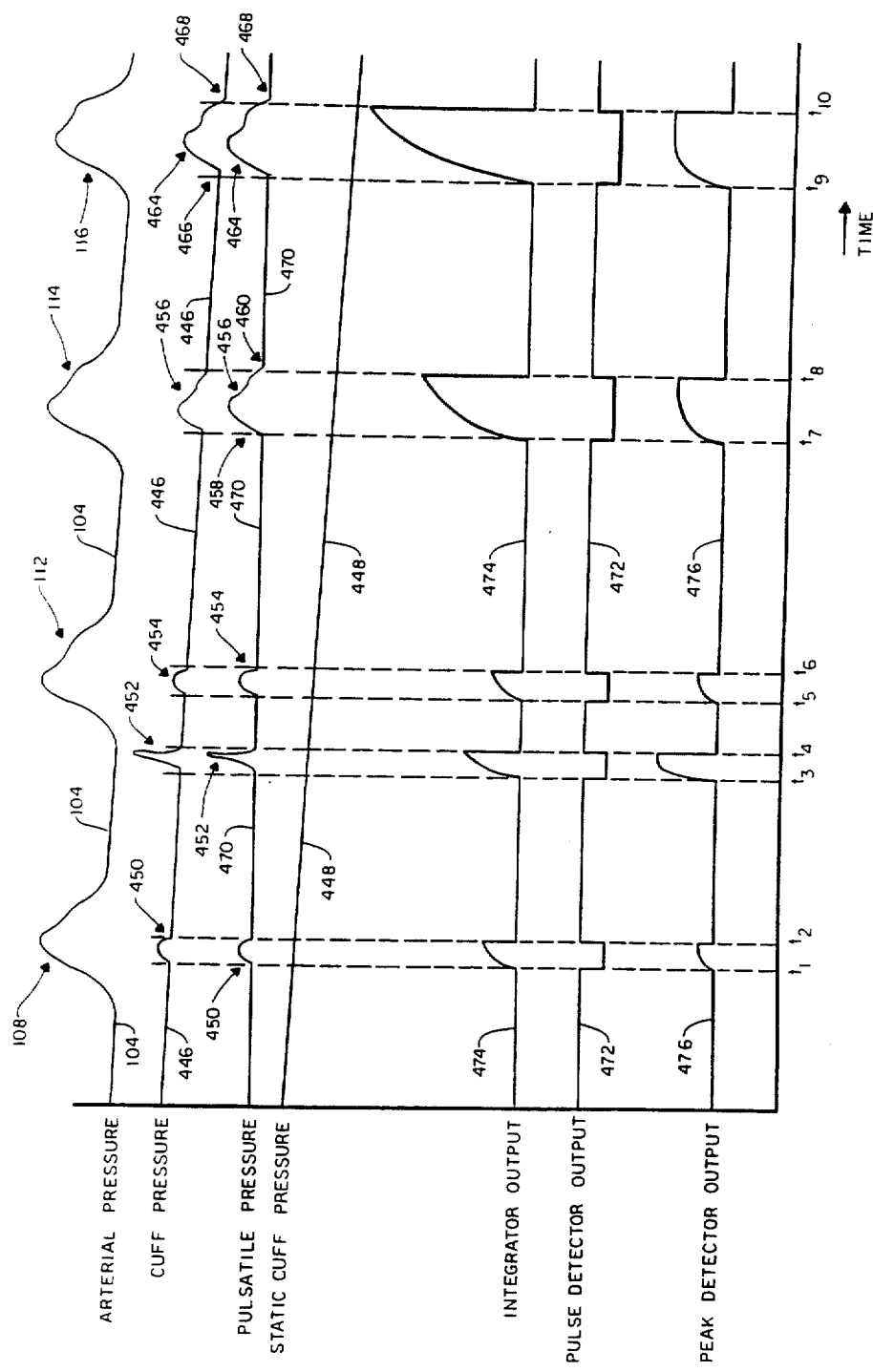
Figure 2:
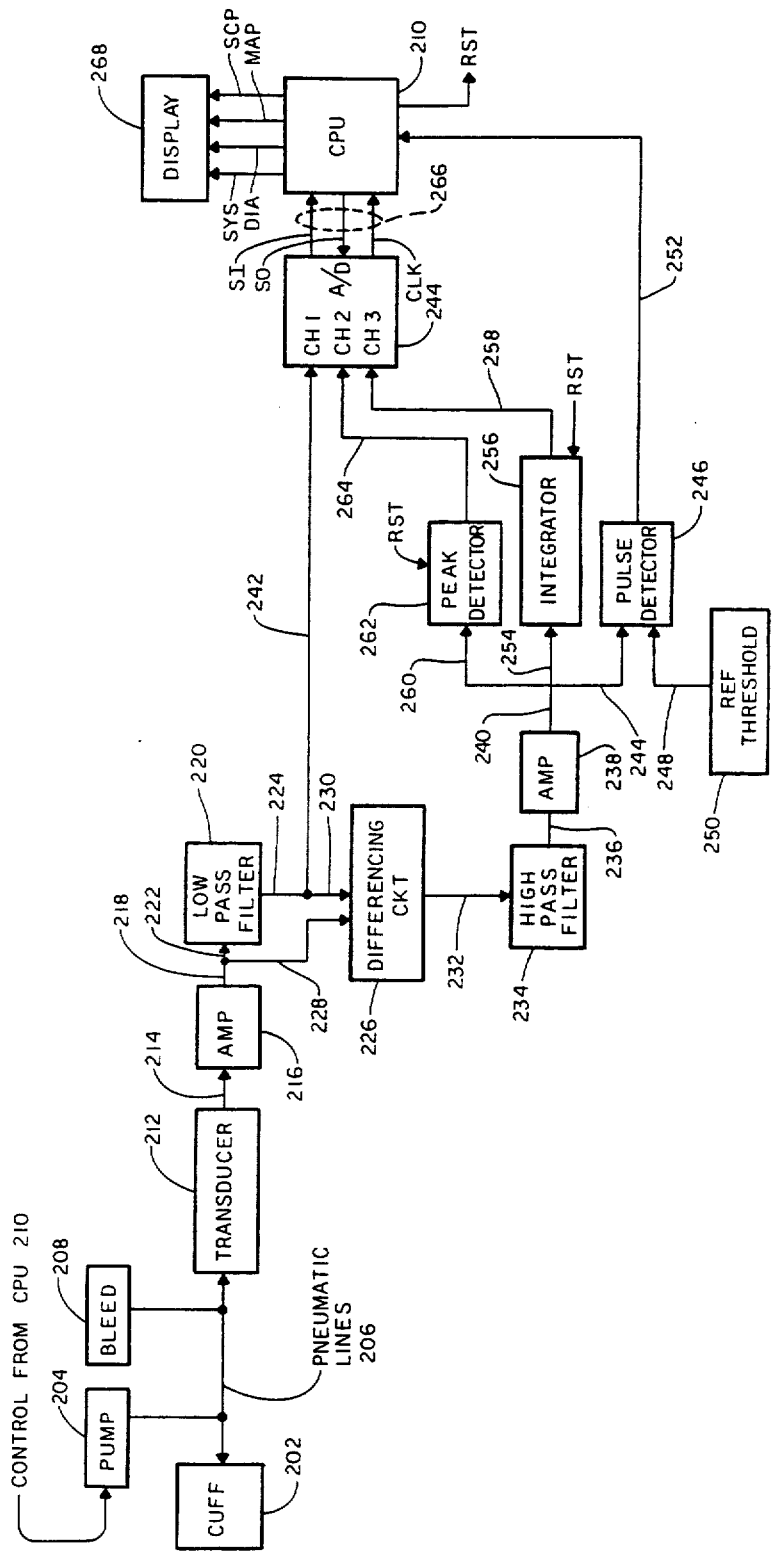

When the cuff pressure has been inflated to a sufficiently high value, the inflation action of the pump 204 can be ceased, and the deflation cycle can be commenced. In the particular embodiment illustrated in FIG. 2, the deflation cycle is essentially continuous, with air escaping from the cuff 202 through the bleed device 208. The pressure transducer 212 is responsive to the pressure in pneumatic line 206 for generating an analog electrical signal on line 204 which is linearly proportional to the pressure detected in pneumatic line 206. For purposes of illustration and explanation, an exemplary waveform 446 is illustrated in FIG. 9, which represents the analog signal on line 214 corresponding to the cuff pressure, as a function of time. The pressure transducer 212 is conventional in design and any of numerous types of commercially available transducers can be employed with the measuring device 200 in accordance with the invention.

As also previously described with respect to FIG. 2, the analog signal on line 214, representing the instantaneous cuff pressure, is applied as an input signal to a conventional amplifier 216. The amplifier 216 operates to amplify the cuff pressure signal for purposes of subsequent processing. The amplifier 216 is conventional in design and can comprise any of numerous commercially available amplifier. For example, the amplifier 216 can include a conventional inverting operational amplifier in a circuit combination with input and feedback resistors. In addition, an offset adjustment potentiometer or similar circuitry can be utilized for adjusting the gain and offset of the amplifier 216.

As also previously described with respect to FIG. 2, the amplified analog output signal of the amplifier 216 on line 218 is applied as an input signal on line 222 to low pass filter circuit 220. The low pass filter circuit 220 essentially removes the pulse components from the analog signal and applies, as an output signal on line 224, an analog signal representative only of the static cuff pressure. This signal is illustrated as static cuff pressure waveform 448 in FIG. 9. The low pass filter circuit 220 is also conventional in design and can, for example, comprise a conventional configuration of an operational amplifier, input resistors, and a parallel feedback configuration of a resistor and capacitor.

Figure 1:
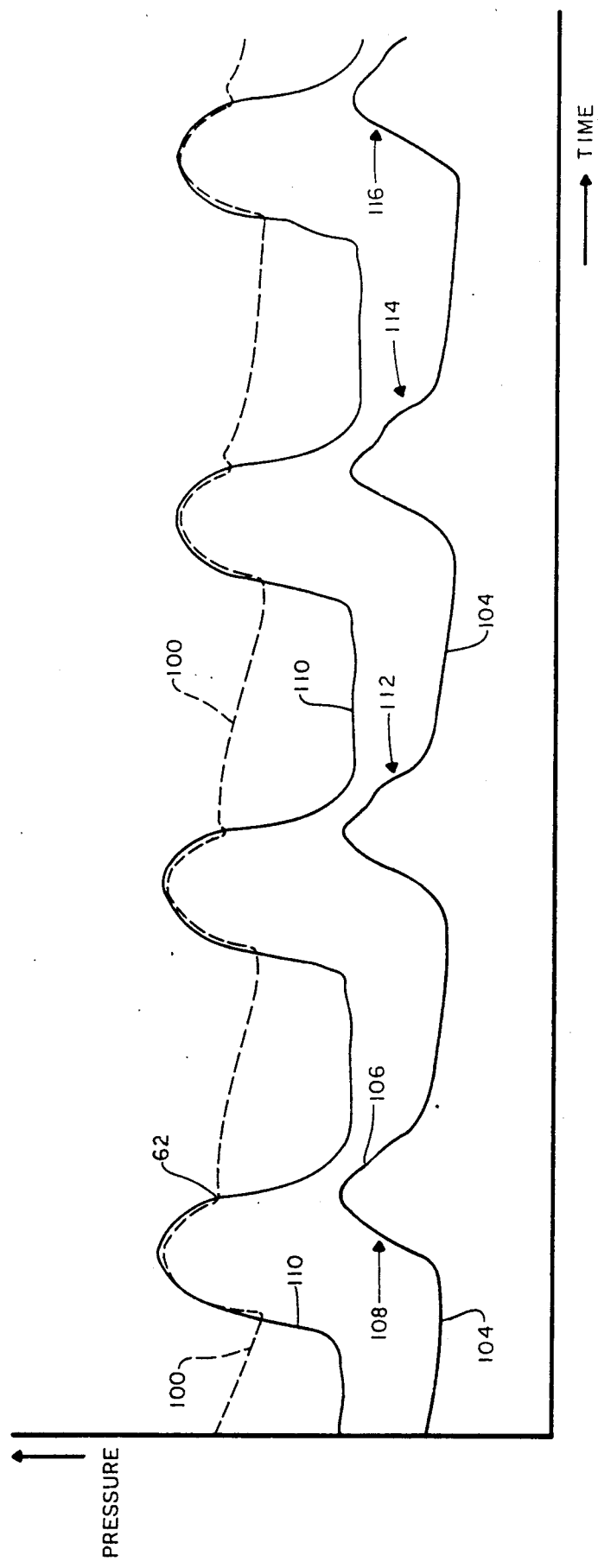
FIG. 1 is a prior art representation of waveforms illustrating aortic, arterial and left ventricular pressure wave forms during heart activities.

For purposes of illustration and explanation of the blood pressure measuring device 200, a deflation cycle associated with the measuring device 200 is assumed to initially generate the cuff pressure waveform 446 as previously described and shown in FIG. 9. As also previously described, as the cuff is deflated, static cuff pressure will decrease as shown by the static cuff pressure waveform 448. Even though the brachial artery is, at least, partly occluded after the cuff is only slightly deflated, pressure will still build up in the brachial artery due to the onset of arterial blood pressure pulses. Such a blood pressure pulse is illustrated in FIG. 1 as arterial blood pressure pulse 112. The brachial artery will expand at the proximal end of the cuff due to the onset of the arterial pressure pulse, but the artery is still sufficiently closed to prevent blood from flowing past the cuff. Nevertheless, the pressure transducer 212 will still detect the pressure change in the cuff caused by the expansion of the brachial artery. With reference to FIG. 9, this pressure change in the cuff is shown as a first pulsatile pressure signal 450. As the cuff continues to deflate, and as previously described herein, movement of the arm (i.e., by flexing muscles around the brachial artery, for example) can create pressure changes (commonly referred to as "motion artifacts") that will also be detected by the transducer 212. An illustration of such a motion artifact is shown as the second pulsatile pressure signal 452 in FIG. 9.

As the cuff pressure continues to decrease to the pressure where blood corpuscles can just barely pass through a relatively tiny opening in the brachial artery under the cuff, the arterial pressure pulse 112 shown in FIG. 1 will create a third pulsatile pressure signal or pulse 454, again which will be detected by pressure transducer 212. The cuff will then further deflate to a point where the brachial artery is substantially forced open when the arterial pressure, such as that shown in FIG. 1 as arterial pressure pulse 114, exceeds the static cuff pressure. As illustrated in FIG. 9, this arterial pressure pulse 114 will result in a fourth pulsatile pressure signal 456, which exceeds the static cuff pressure between the first cuff pressure point 458 and the second cuff pressure point 460. Between these first and second cuff pressure points 458 and 460, respectively, the pressure in the cuff is such that the partially occluded artery opens abruptly at the first cuff pressure point 458, thereby allowing blood to flow freely in the artery under the cuff. However, the artery becomes partially occluded again, after the second cuff pressure point 460. While the artery is open, blood flows past the cuff in such a way that the fourth pulsatile pressure signal 456 is not distorted since, for example, there is no reflection of blood which would be caused by an occluded artery. That is, the waveform of the fourth pulsatile pressure signal 456 resembles, at least, a portion of the waveform of arterial pressure pulse 114.

As the cuff pressure further deflates, the next pulsatile pressure signal, illustrated in FIG. 9 as the fifth pulsatile pressure signal 464, substantially resembles more of the waveform of arterial pressure pulse 116, which actually created the fifth pulsatile pressure signal 464. In this case, blood is permitted to flow freely through the brachial artery for a longer period of time, since the length of time between the third cuff pressure point 466 and the fourth cuff pressure point 468 is larger than the length of time between first and second cuff pressure points 458 and 460, respectively. That is, the arterial blood pressure exceeds the cuff pressure for a longer period of time. For purposes of further illustration and explanation, the onset of the first pulsatile pressure signal 450 is illustrated in FIG. 9 as occurring at time $t_1$, and essentially ceasing at time $t_2$. Correspondingly, second pulsatile pressure signal 452 is assumed to commence at time $t_3$ and end at time $t_4$. Likewise, the third, fourth and fifth pulsatile pressure signals 454, 456 and 464 are assumed to commence at times $t_5$, $t_7$ and $t_9$, respectively. Each of these pulsatile pressure signals is also assumed to cease at times $t_6$, $t_8$ and $t_{10}$, respectively.

Referring again to FIG. 2, the static cuff pressure appearing as an analog signal on line 224 is represented by the static cuff pressure waveform 448 in FIG. 9. In the particular blood pressure measuring device 200 described herein, this pressure waveform 448 will be substantially a linearly decreasing signal.

As also previously described with respect to FIG. 2, the signal on line 228, representing the combined static and pulsatile pressures (and substantially illustrated as cuff pressure waveform 446 in FIG. 9) is applied as an input signal to the "+" terminal of differencing circuit 226. Correspondingly, the analog signal on line 224, representing only the static cuff pressure, is applied as an input signal through line 230 to the "−" terminal of differencing circuit 226. The differencing circuit 226 operates so as to essentially subtract the magnitude of the static cuff pressure waveform 448 from the total cuff pressure waveform 446. The resultant output of the differencing circuit 226, applied as an output signal on line 232, represents only the pulsatile cuff pressure, and is substantially illustrated as pulsatile cuff pressure waveform 470 in FIG. 9.

In view of the practical physical realization of the circuit configuration illustrated in FIG. 2, the actual analog signal on line 232 will include a DC component, along with the pulsatile pressure signals. For purposes of removing the DC component, the analog signal on line 232 is applied as an input signal to the high pass filter circuit 234. The resultant output signal on line 236 represents the pulsatile cuff pressure analog signal, with all DC components removed. In practical effect, the high pass filter can be physically realized substantially as a series capacitor.

As further previously described, the pulsatile cuff pressure signal, represented by waveform 470 in FIG. 9, after removal of all DC components via the high pass filter 234, is applied as an input signal from line 236 to the second amplifier 238 as shown in FIG. 2. The resultant amplified pulsatile cuff pressure signal is applied as an output signal on line 240. The second amplifier 238 is also conventional in design, and can include, for example, a conventional arrangement comprising a non-inverting operational amplifier, shunt capacitor, and series and feedback resistors.

As also previously described with respect to FIG. 2, the pulsatile cuff pressure signal on line 240 is applied as an input signal from line 244 to the pulse detector circuit 246. Also applied as an input signal to the pulse detector circuit 246 is a reference threshold signal from reference threshold circuit 250 on line 248. An exemplary output signal of the pulse detector circuit 246, which appears on line 252, is illustrated in FIG. 9 as pulse detector waveform 472. In one exemplary embodiment of the pulse detector circuit 246, the pulse detector output signal on line 252 can remain in a "high" state at all times when the pulsatile cuff pressure signal on line 244 is less than the reference threshold signal on line 248. However, when the pulsatile cuff pressure signal on line 244 exceeds the reference threshold signal on line 248, the output of the pulse detector circuit 246, on line 252, will switch to a "low" state. This output signal will remain in the low state until such time as the reference threshold signal again exceeds the pulsatile cuff pressure signal. The primary purpose of the reference threshold signal is to provide a bias to the detection circuitry, such that the pulse detector circuit 246 will not provide output signals indicative of the existence of pulses merely because of noise signals or the like associated with the pulsatile cuff pressure signal on line 244. Referring to FIG. 9, the pulsatile cuff pressure waveform 470 includes a pulse 450 commencing substantially at time $t_1$. Assuming that the value of the reference threshold signal on line 248 is relatively low, the pulse detector circuit 246 will operate so as to switch states of the pulse detector output waveform 472 at a time substantially equal to time $t_1$. Correspondingly, with the pulse 450 ending at a time substantially equal to time $t_2$, the pulse detector output waveform 472 will switch from a low state to a high state substantially at time $t_2$. Similar state switches of pulse detector output waveform 472 are illustrated in FIG. 9 for pulses 452, 454, 456 and 464.

With the pulse detector output signal on line 252 is applied as an input signal to the CPU 210, the CPU 210 will operate so as to detect the state switch from a high state to a low state of the pulse detector output waveform 472. In response to the switching from a high state to a low state, the CPU 210 will operate so as to switch the state of the reset signal RST so as to enable the previously described integrator circuit 256 and peak detector circuit 262. When the enabling state of the reset signal RST is applied to the integrator circuit 256, the particular pulse appearing within the pulsatile cuff pressure signal on line 254 (the input to the integrator circuit 256) is integrated by circuit 256. The resultant integral output signals are applied on line 258, and are illustrated in FIG. 9 as integrator output waveform 474.

Correspondingly, and also as previously described with respect to FIG. 2, the peak detector circuit 262 will operate so as to generate an output signal on line 264 corresponding to the maximum or peak amplitudes of each of the pulses detected by pulse detector circuit 246. Such exemplary peak amplitude signals for each of the pulses 450, 452, 454, 456 and 464 are illustrated in FIG. 9 as peak detector output waveform 476. In summary, each pulsatile pressure signal within the pulsatile signal waveform 470 will be detected by pulse detector 246. As a result, each pulsatile pressure signal will be integrated by integrator circuit 256 and the maximum amplitude of each pulsatile pressure signal will be determined by peak detector 262.

As also previously described, the integrator output signal on line 258 will be applied as an input signal on channel CH3 to the A/D converter circuit 244. Correspondingly, the maximum amplitude detected for each pulse, appearing as an output signal from the peak detector circuit 262 on line 264, will be applied as an input signal to the A/D converter circuit 244 on channel CH2. In addition to these signals, the static cuff pressure, illustrated in FIG. 9 as static cuff pressure waveform 448 and appearing on line 242, is applied as an input signal to the A/D converter circuit 244 on channel CH1. As will be described in subsequent paragraphs herein, for each of the pulses detected by the pulse detector circuit 246, the CPU 210 will operate so as to apply signal codes to the A/D converter circuit 244 on line SO. The signal codes will effectively request the A/D converter circuit 244 to convert the analog signals appearing on channels CH1, CH2 and CH3 into digital signal representations and apply these digital signals to the CPU 210 in a serial format over line SI.

As also previously described, and as will be described in greater detail herein, the CPU 210 will receive the peak amplitude and integral for each pulse, and effectively subtract the digital representation of the peak amplitude signal from the digital representation of the integral for each pulsatile pressure signal, thereby producing a difference signal. A particular algorithmic process can then be utilized so as to determine the particular pulses corresponding to static cuff pressures equivalent to systolic, diastolic and mean arterial pressures. In accordance with the invention, and unlike various prior art oscillometric blood pressure monitors, it is unnecessary to "wait" until the entire deflation cycle is completed, prior to determining the static cuff pressure as corresponding to systolic, diastolic and mean pressures. That is, at the time of occurrence of a pulse, the blood pressure measuring device 200 in accordance with the invention will determine whether or not the static cuff pressure occurring substantially at the time of occurrence of the pulse is equivalent to the systolic or diastolic pressures. That is, the systolic and diastolic pressures will be determined in a "real time" mode, thereby negating any requirement for maintaining data tables or the like comprising pulse characteristics for each pulse detected during the entire pressure deflation cycle. Further, not only is it unnecessary to maintain data tables comprising pulse characteristic data, but it is also unnecessary to maintain any data tables representative of static cuff pressures for each of the detected pulses.

Figure 6:
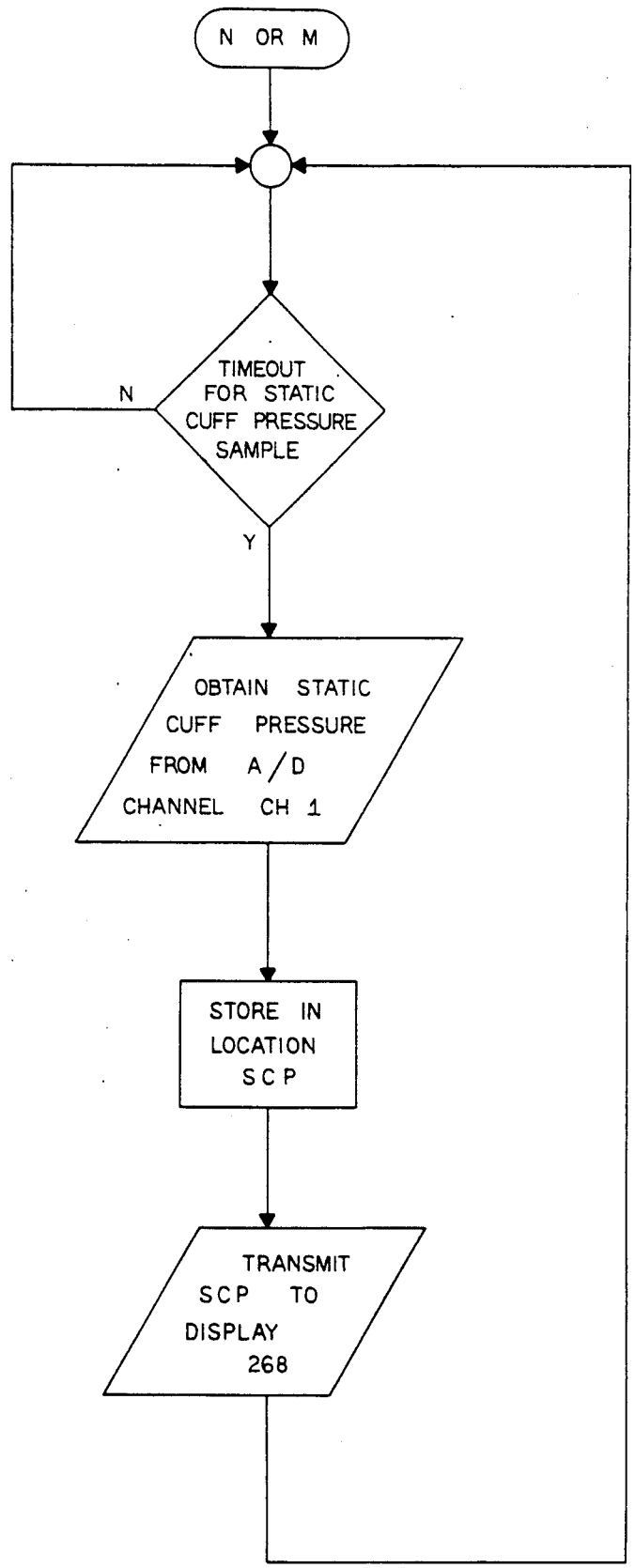
FIG. 6 is a representative sequence diagram for periodically obtaining static cuff pressures.

An exemplary embodiment of the functional operations which may be performed by CPU 210 in accordance with the invention will now be described with reference to the functional sequence diagrams illustrated in FIGS. 6, 7 and 8. As previously described, these functional operations may be performed primarily by means of computer software. However, all operations described herein could, if preferred, be physically realized by means of analog and/or digital circuitry. Also, the particular functional sequences described in subsequent paragraphs herein should not, in any manner, be considered the only means by which to perform the primary functions in accordance with the invention. Numerous other process sequences can be utilized without departing from the principal novel concepts of the invention.

First, for purposes of obtaining the static cuff pressures, the CPU 210 can operate so as to periodically "sample" the static cuff pressure appearing at the input channel CH1 of the A/D converter circuit 244. FIG. 6 illustrates a simplified functional sequence diagram for performing this task. As shown in FIG. 6, the functional sequence can be characterized as being initiated at sequence location NORM. This particular sequence is assumed to be performed during the deflation cycle, when the static cuff pressure is decreasing. Prior to initiating this deflation cycle, and as previously described herein, the cuff can be inflated by sending appropriate signals from the CPU 210 to the pump 204 illustrated in FIG. 2. As also previously described, various functional tests can be performed so as to assure that the cuff has been inflated to a pressure substantially above the systolic pressure. For example, if a pulse is detected within a predetermined time period or, alternatively, within a certain minimum decrease in pressure from the maximum cuff pressure at the initiation of the cycle, the cycle may be aborted and restarted, with the initial cuff pressure being initiated to a value higher than the previous initial maximum pressure. Other alternative types of tests, so as to insure that the initial cuff pressure is substantially above the systolic pressure, can also be utilized. All of these types of tests can be performed by functional operations within the CPU 210, with signal communications with the pump 204.

Returning to FIG. 6, during the deflation cycle, the static cuff pressure from the A/D converter circuit 244 can be sampled periodically. For example, utilizing an internal clock within the CPU 210, a "time out" sequence or similar arrangement can be utilized, whereby functions can be performed within the CPU 210 so as to obtain a then current reading of the static cuff pressure. The periodicity for such readings should be sufficient so that a static cuff pressure reading which occurs prior to initiation of a pulse will be sufficiently "close" to the static cuff pressure occurring at the time of the pulse, so that the prior reading can be utilized as the then current cuff pressure. For example, static cuff pressure could be read every 0.1 seconds with a pressure deflation rate in the range of 2 to 6 mm Hg per second. This rate of deflation, in combination with the sampling rate, provides a resolution of at least 0.6 mm Hg.

Returning again to FIG. 6, when the "time out" period for reading a static cuff pressure sample has occurred, functional operations can be performed for purposes of obtaining the static cuff pressure reading. With reference to FIG. 2, the functional operations associated with obtaining a reading of the static cuff pressure can include the application of appropriate signal codes as output data signals on line SO. These data codes are applied as input signals to the A/D converter circuit 244, with the converter circuit 244 being responsive to the codes so as to convert the analog signal appearing at channel CH1 (corresponding to the static cuff pressure on line 242) into a digital data signal applied to line SI in serial format as output data signals. Clock pulse signals on line CLK can be utilized for purposes of decoding the binary data pulses.

Referring again to FIG. 6, the CPU 210 can be responsive to the reception of these digital data signals so as to store the then current reading of the static cuff pressure in a data memory location SCP. Correspondingly, if desired, the static cuff pressure reading can be transmitted as output data signals on line SCP (FIG. 2) so as to display the static cuff pressure on the visual display 268. Following the transmittal of the static cuff pressure to the display 268, the functional sequence within the CPU 210 can reset the time out clock for reading of the static cuff pressure, and again go into a "wait" state until a subsequent time out occurs for purposes of obtaining another reading of the static cuff pressure.

It should be emphasized that, in accordance with the invention, the data memory location SCP is not required to be greater in size than necessary for storing only one reading of the static cuff pressure. That is, in accordance with the invention, it is unnecessary to maintain readings of static cuff pressures for each sample or for each detected pulse. Again, the blood pressure measuring device 200 in accordance with the invention operates in a "real time" mode, and does not require any substantial storage of data or any substantial post processing of data following the entirety of a deflation cycle.

For purposes of obtaining and operating on pulse characteristics when pulsatile pressure signals are detected by the pulse detector 246, various types of functional sequences can be employed. For example, the software sequences executed in the CPU 210 can periodically interrogate the pulse detector output signal on line 252, which is applied as an input signal to the CPU 210. As previously described, when this signal on line 252 changes from a high state to a low state, a pulse has been detected. Correspondingly, upon the occurrence of a state switch from the low state to the high state, the pulse is assumed to have ended. The functional operation sequences within the CPU 210 can be responsive to the initiation and completion of a pulse, as indicated by the signal on line 252, for purposes of obtaining and operating on the pulse characteristics.

Alternatively, it would also be possible to utilize a conventional "interrupt" sequence, whereby a switch of the signal on line 252 from a high state to a low state will cause an interrupt of the then operational software sequences within the CPU 210. In such event, functional software control can be switched to an operational sequence such as that illustrated in FIG. 7, and identified as the "INTERRUPT" sequence. Referring specifically to FIG. 7, when the occurrence of a pulse has been detected, and operational control of the software functions in the CPU 210 have been switched to the INTERRUPT sequence, the signal on line 252 can be periodically interrogated so as to determine when the pulse is complete. To ensure appropriate operation, a maximum time duration for a pulse may be assumed. In the event the total time period between initial detection of the pulse and the then current time exceeds the maximum assumed pulse duration, operational control can be transferred to an "abort" sequence, whereby appropriate actions could be undertaken so as to abort the current deflation cycle or, alternatively, ignore the characteristics of the current pulse.

Assuming that the pulse has been completed, as indicated by the pulse detector output signal on line 252, appropriate reset signals RST can be generated by the CPU 210 and applied to the integrator circuit 256 and peak detector circuit 262 as previously described herein with respect to FIG. 2. The purpose of applying the reset signals is to inhibit operation of these circuits until the occurrence of the next pulse. As apparent from the foregoing, the selective application of the "enable" or "inhibit" states of the reset signals RST can be dependent on signals from pulse detector circuit 246 indicating the presence or absence of a pulse.

Following application of the reset signals, a determination can be made as to whether the peak amplitude of the current pulse is greater than the maximum amplitude of any previously occurring pulse. In the event the peak amplitude of the current pulse exceeds the amplitude of any previously occurring pulse, the then current reading of the static cuff pressure in data memory location SCP can be stored in data memory location MAP. The purpose for these functional operations is to obtain a determination of the static cuff pressure corresponding to the mean arterial pressure. In this particular sequence, the mean arterial pressure is assumed to correspond to the static cuff pressure occurring at or near the time of occurrence of the pulse of maximum amplitude throughout the deflation cycle. Again, it should be noted that data memory location MAP need comprise only sufficient storage for storing one reading of a static cuff pressure. That is, the static cuff pressures corresponding to each of the prior pulses need not be saved in memory. Further, it should be emphasized that the particular process, whereby the pulsatile pressure signal of maximum amplitude is assumed to substantially correspond to the time of occurrence of the static cuff pressure corresponding to the mean arterial pressure represents only one embodiment of a algorithm which can be utilized to determine mean arterial pressure. Other algorithmic processes can also be utilized. However, the concept of assuming the static cuff pressure at the time of occurrence of the maximum amplitude pulse to be the mean arterial pressure is relatively well known and used in other types of prior art blood pressure measuring devices.

Following a determination as to whether the peak amplitude of the current pulse represents the pulse of maximum amplitude to have yet occurred, a difference signal computation can be made. As previously described, the difference signal represents a subtraction of the peak amplitude of the then current pulse from the integral value of the pulse.

Following a computation of the difference signal for the then current pulse, a determination can be made as to whether the systolic pressure has already been obtained. For this purpose, for example, a flag bit or similar data indication can be utilized for purposes of indicating when the systolic pressure is determined.

Figure 7A:
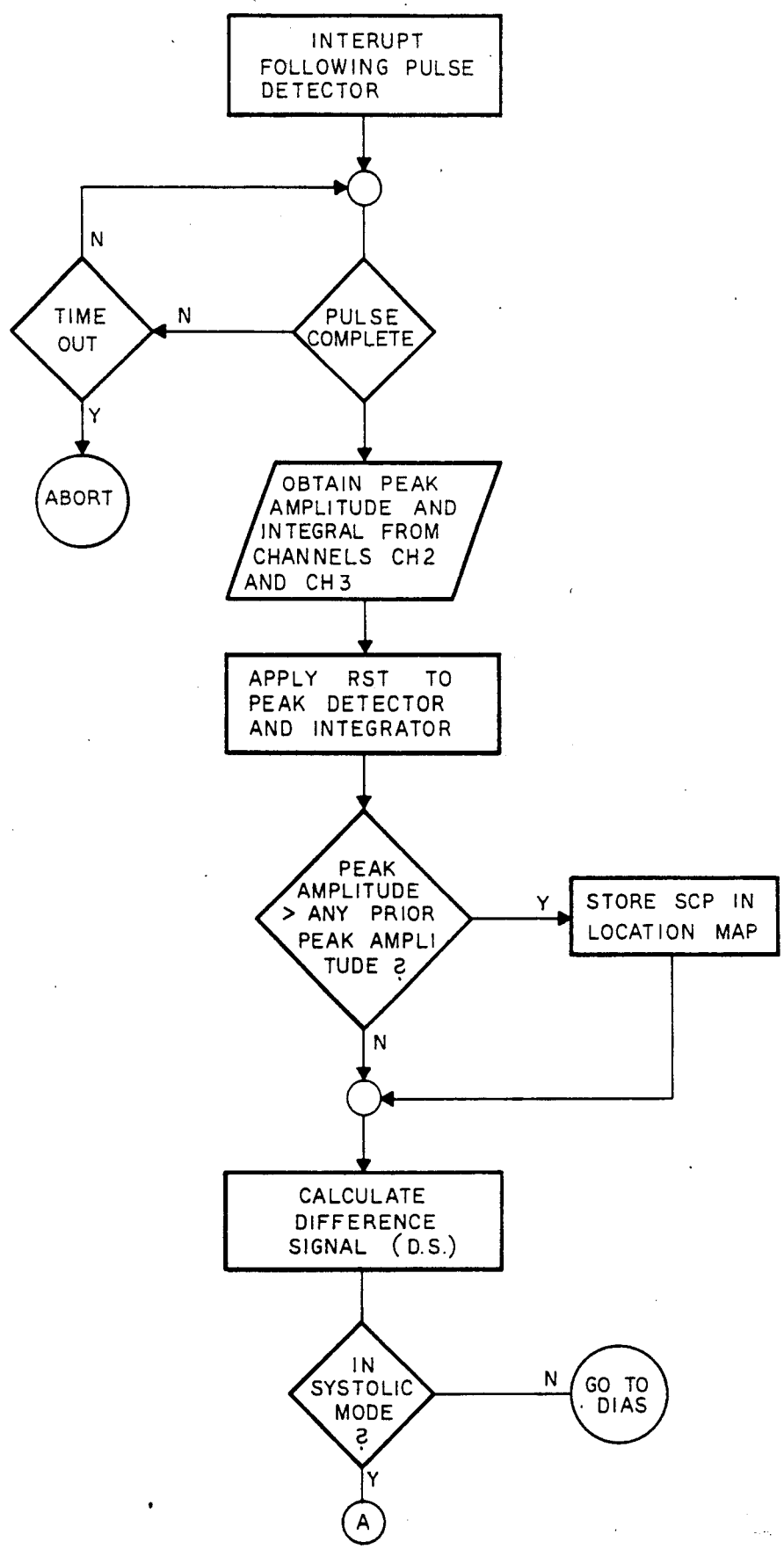
FIG. 7A and 7B are a representative sequence diagram for a sequence of functions which may be performed in accordance with the invention for purposes of determining systolic blood pressure.
Figure 7B:
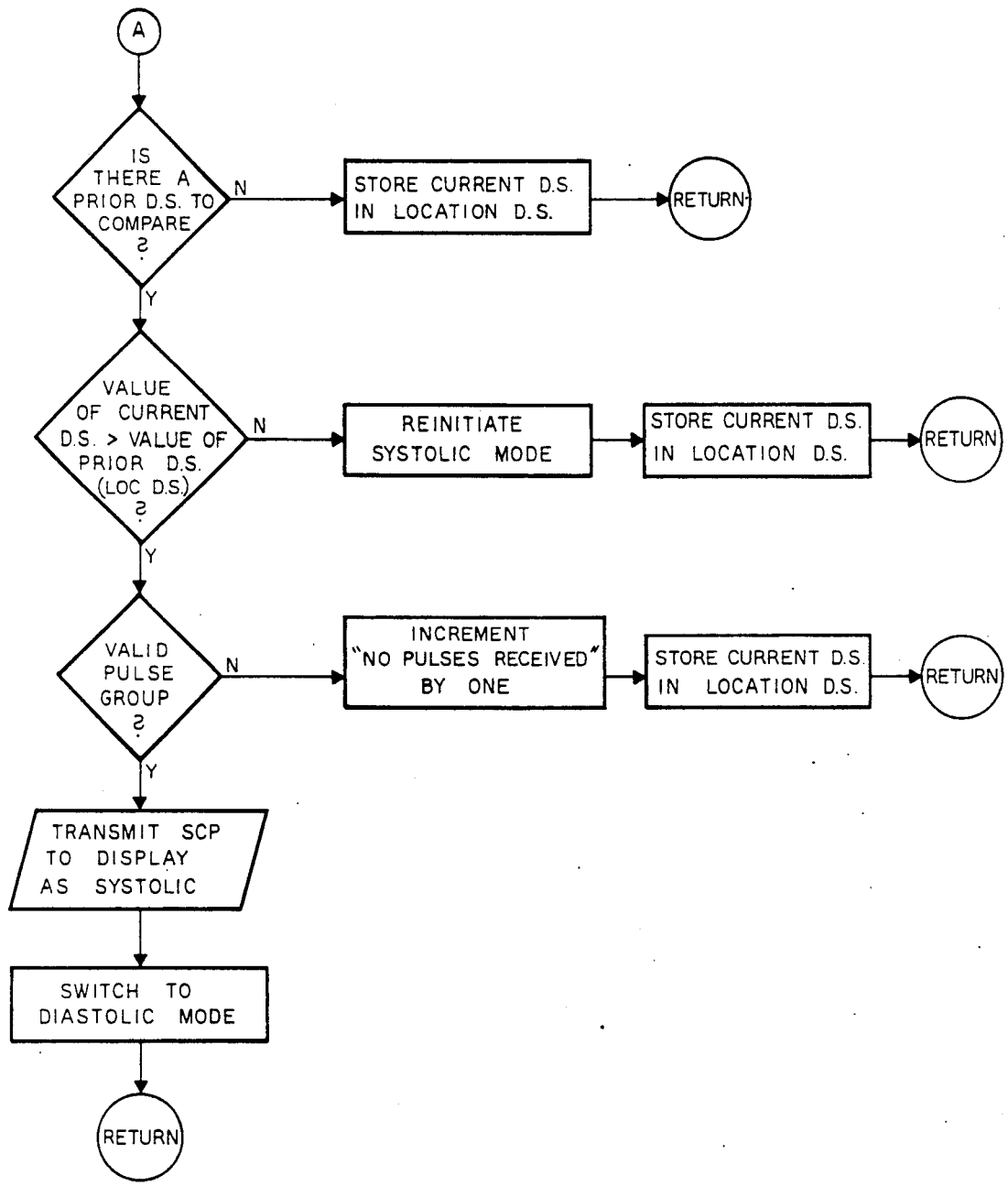

Continuing to refer to FIG. 7, and assuming that a systolic pressure has not yet been determined (shown in FIG. 7 as being indicated by the sequential operation still being in the "systolic mode"), a particular algorithmic process can be employed, utilizing the difference signals, for determining if the static cuff pressure corresponding to the occurrence of the then current pulse is representative of the systolic pressure. The following paragraphs describe a particular algorithmic process which can be utilized for determination of whether systolic pressure has occurred. However, it should be emphasized that other algorithmic processes may also be utilized for this determination, without departing from the primary concepts of the invention.

In the particular algorithmic process described with respect to FIG. 7, comparisons are made between magnitudes of difference signals of successively occurring pulses. Accordingly, a determination is first made as to whether the difference signal computed with respect to the then current pulse should be compared with the magnitude of the difference signal of an immediately previously occurring pulse. If, because of the particular algorithmic process utilized, the current pulse represents the "first" pulse in a sequence of successive pulses to be analyzed, this difference signal can be stored in data memory location DS. Following storage of the magnitude of this difference signal, control of the sequential operations of CPU 210 can be transferred from the INTERRUPT sequence back to the normal operational sequence.

In the event the magnitude of the difference signal associated with the immediately previously occurring pulse is representative of a pulse of a potentially valid "pulse group," the magnitude of the difference signal of the then current pulse can be compared to the magnitude of the difference signal associated with the immediately previously occurring pulse.

In the particular algorithmic process illustrated in FIG. 7, a valid "pulse group" is assumed to have occurred if the magnitudes of difference signals associated with a predetermined number of consecutively occurring pulses continues to increase. In such event, the most recent static cuff pressure reading obtained prior to occurrence of the then current pulse is assumed to correspond to the systolic pressure. Referring again specifically to FIG. 7, in the event the magnitude of the difference signal of the then current pulse is not greater than the magnitude of the difference signal associated with the prior pulse, it is assumed that a valid pulse group has not yet been obtained, and the determination of a valid pulse group must be reinitiated, with the then current pulse assumed to correspond to the first pulse of a potentially valid pulse group. Accordingly, various functional operations can be undertaken so as to "reinitiate" the determination of the valid pulse group, including the storage of the magnitude of the difference signal of the then current pulse into data memory location DS. Thereafter, sequential control can be returned to the normal operating sequence of CPU 210.

Conversely, in the event the magnitude of the difference signal of the then current pulse is greater then the magnitude of the difference signal of the prior pulse, a determination can be made as to whether a sufficient number of consecutive pulses have been obtained, wherein the difference signals associated with the successive pulses have continued to increase in magnitude. In the event such predetermined number of pulses have not yet occurred, the magnitude of the difference signal of the then current pulse can be stored in data location DS. Correspondingly, a data word indicative of the current number of pulses which have been received within the potentially valid pulse group can be incremented by one. Thereafter, sequential control can be returned to the normal operating sequence of CPU 210.

In the event that a sufficient number of pulses have been obtained so as to indicate a valid pulse group, the most recent sample of the static cuff pressure (previously stored in data memory location SCP) can be assumed to correspond to the systolic pressure. Accordingly, data from data memory location SCP can be applied as an output signal on line SYS (FIG. 2) and transmitted to the display device 268. In this manner, in a "real time" mode, the systolic pressure is immediately displayed upon the occurrence of the pulse corresponding to the systolic pressure.

As further shown in FIG. 7, following the optional transmittal of the systolic pressure indication to the display device 268, appropriate flag bits or the like can be switched so as to indicate that the algorithmic process should now analyze the pulse characteristics for purposes of determining diastolic pressure. Thereafter, sequential control can again be returned to the normal operating sequence.

Figure 8:
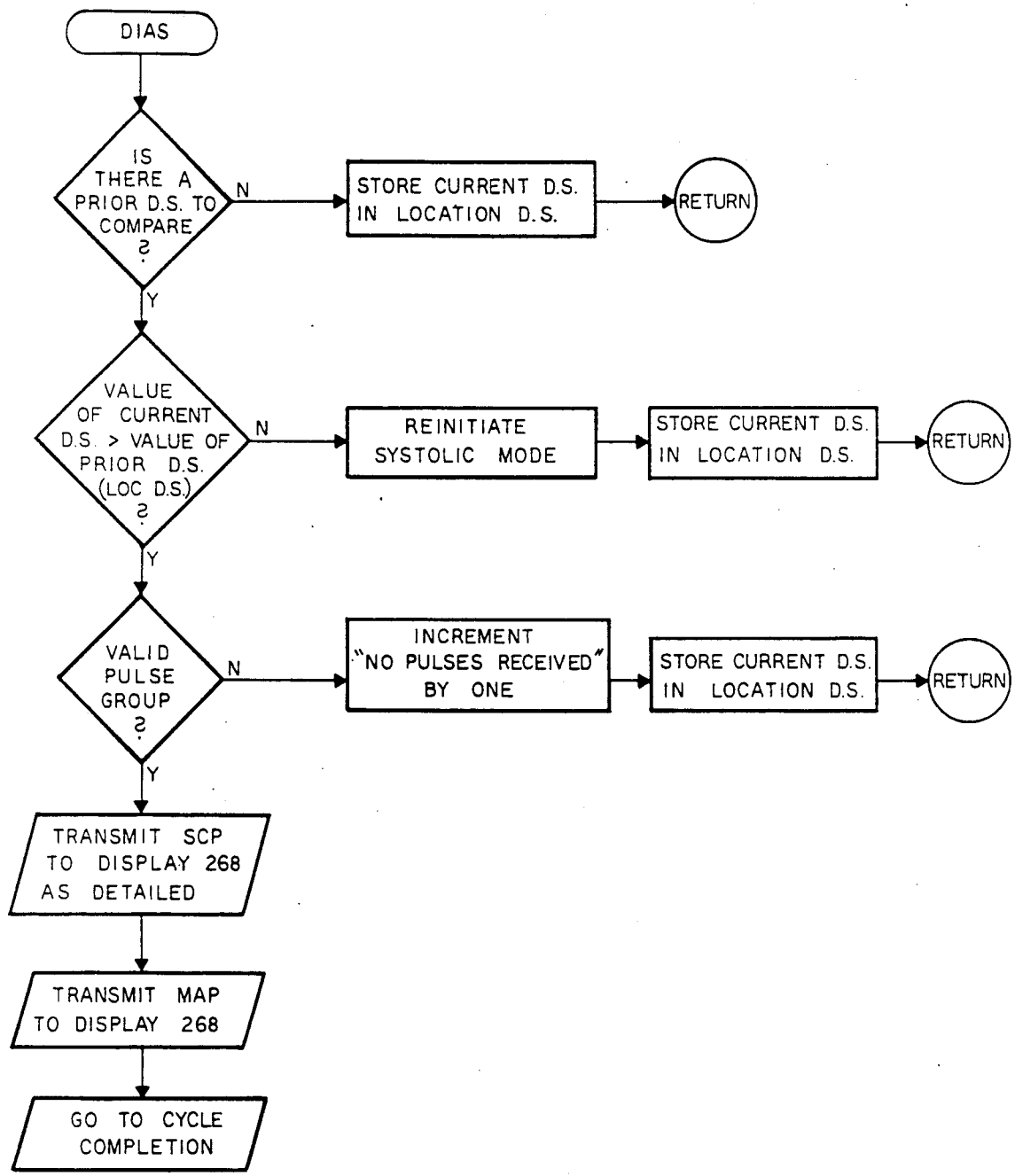
FIG. 8 is a representative sequence diagram of certain functions which may be performed in accordance with the invention for purposes of determining diastolic blood pressure.

FIG. 8 is a simplistic sequence diagram illustrating a possible functional sequence for determination of diastolic pressure. With reference first to FIG. 7, when an interrogation of appropriate flag bits indicates that sequential operation is in the "diastolic mode," sequential program control can be transferred to the functional sequence identified as sequence DIAS illustrated in FIG. 8. As shown in FIG. 8, and as previously described with respect to the determination of systolic pressure as illustrated in FIG. 7, a determination can first be made as to whether the difference signal associated with the current pulse should be compared with the magnitude of the difference signal associated with an immediately previously occurring pulse. If not, the magnitude of the current difference signal is stored in data memory location DS and a return is made to the normal program sequence.

If a comparison should be made (indicating that the immediately prior pulse is a pulse of a potentially valid pulse group), a somewhat different algorithmic process can be utilized to determine diastolic pressure. For purposes of determining diastolic pressure, a "valid pulse group" can be assumed to be a pulse group wherein the magnitudes of the difference signals associated with a predetermined number of successively occurring pulses continues to decrease. Accordingly, as shown in FIG. 8, a determination can be made as to whether the magnitude of the difference signal of the current pulse is less than the magnitude of the difference signal associated with the prior pulse. If the magnitude of the current difference signal is not less than the magnitude of the difference signal associated with the prior pulse, it could be assumed that the prior pulse is not a pulse of a valid pulse group. Accordingly, the magnitude of the current difference signal can be stored in data memory location DS, and appropriate data indicators can be reset so as to indicate that the current pulse is either not a member of a valid pulse group or, alternatively, is the first pulse of a potentially valid pulse group. Sequential control can then be returned to the normal operating sequence.

In the event the magnitude of the difference signal of the current pulse is less than the magnitude of the difference signal of the prior pulse, a determination can be made as to whether a sufficient number of pulses meeting the appropriate criteria have occurred in succession. If a sufficient number of pulses meeting the appropriate criteria has not yet been detected, the magnitude of the difference signal of the current pulse is stored in data memory location DS, and an appropriate data word representative of the number of pulses currently received in the potentially valid pulse group can be incremented by one. Sequential control is then returned to the normal operating sequence.

In the event a sufficient number of pulses has been received, which meet the appropriate criteria with respect to the difference signals, a "valid pulse group" is assumed to have been received. The most recent sample of the static cuff pressure (previously stored in data memory location SCP) can then be assumed to correspond to the diastolic pressure. Accordingly, the static cuff pressure can be transmitted as an output signal and applied from line DIAS to the display device 268, for purposes of visually displaying the diastolic pressure. Again, as with the systolic pressure, a determination has been made in a "real time" mode of the diastolic pressure, without requiring any "post processing" of stored data following the entirety of a deflation cycle. That is, the diastolic pressure is immediately indicated at the visual display device 268 upon occurrence of a pulse which occurs substantially at or near the time of occurrence of the static cuff pressure corresponding to the diastolic pressure.

Following the determination of diastolic pressure, and as further shown in FIG. 8, it is possible to also transmit the pressure data previously stored in data memory location MAP to the display device 268 via line MAP. Again, this pressure is representative of the mean arterial pressure.

Following transmittal of the diastolic pressure data and, optionally, data representative of the mean arterial pressure, sequential program control can be transferred to appropriate functions associated with completion of the pressure deflation cycle, since all data has now been obtained. These cycle completion operations can include various processes, and do not form any of the primary concepts of the invention.

In accordance with the foregoing description, determinations of "valid" pulses are made principally on the basis of difference signals computed with respect to each pulse. Again, these difference signals are characterized as values representing the subtraction of the peak amplitudes of the pulses from the corresponding integral values of the pulses. Without going into complex detail, such difference signals can be utilized for purposes of accurately discriminating between pulses corresponding to motion artifacts and "true" pulses corresponding to heartbeats. For example, a pulse resulting from movement of the user's arm or the like may have a relatively short time duration, while being of a relatively high amplitude. Such a pulse is shown, for example, as pulsatile pressure signal 452 in FIG. 9. It is apparent that with such a pulse, the difference signal may be relatively small, since the integral of the pulse may not be substantially greater in magnitude than the peak amplitude of the pulse. In fact, it is possible that the magnitude of the pulse integral may be less than the peak amplitude.

Further, for purposes of determining systolic pressure, it has been found from experimentation that systolic pressure can be accurately determined as corresponding to the static cuff pressure at or near the time of occurrence of a final pulse in a "valid pulse group." The "valid pulse group" is a group of successive pulses where the difference signals continue to increase in magnitude. Correspondingly, for purposes of determining diastolic pressure, it has been determined from experimentation that diastolic pressure can be accurately assumed to correspond to the static cuff pressure occurring substantially at or near the time of occurrence of a final pulse of a "valid pulse group" determined in accordance with a different algorithm. For diastolic pressure, the valid pulse group can be assumed to have occurred when the difference signals of a predetermined number of successive pulses continuously decrease in magnitude.

Although not expressly described herein, the blood pressure measuring device 200 can also include other features. For example, the measuring device 200 can include such features as a removable data memory or the like, for purposes of storing appropriate blood pressure measurements obtained during a series of periodic deflation cycles. For this purpose, the blood pressure measuring device 200 could be continuously "worn" by the user for a predetermined period of time, such as a 12-hour period. The CPU 210 can include additional timing functions whereby blood pressure measurement cycles are periodically initiated.

When blood pressure measurements have been obtained for any given cycle, data representative of these measurements can be stored in an appropriate memory. This memory can be removable such that the memory can be inserted into another computer device for purposes of providing written or graphical information regarding the blood pressure readings. Further, it is also possible to utilize a memory whereby appropriate readout devices can be interconnected to the memory "in place." With such readout devices, the blood pressure measurements stored in the memory can be read out into another computer-related device for purposes of providing the written and/or graphical information.

In addition to the feature of employing a removable memory, other features can also be employed in the device 200. For example, the CPU 210 can be adapted to measure the time durations between consecutive pulses. In this manner, a pulse rate can be calculated and, if desired, signals corresponding to pulse rates can be applied to the visual display 268.

Again, the blood pressure measuring device 200 in accordance with the invention provides several substantial advantages over known blood pressure measuring devices. For example, the use of difference signals for purposes of determining the occurrence of systolic and diastolic pressures can be utilized to accurately discriminate between true blood pressure pulses and artifacts. Further, blood pressure measuring devices in accordance with the invention operate in a real time mode, whereby systolic and diastolic pressure determinations can be immediately determined upon occurrence. Accordingly, there is no requirement of storage of substantial amounts of data representative of pulse characteristics of all of the pulses occurring throughout the deflation cycle. Further, there is no requirement for any substantive post processing of data following the deflation cycle, for purposes of determining systolic and diastolic pressures. These features not only provide accurate blood pressure measurement determinations, but also provide for physical realization of the measurement devices without requiring complex circuitry, substantial computer memory or substantial software computations.

It should also be apparent that the principles of the invention are not limited to the specific blood pressure measuring device described herein for determining systolic and diastolic pressures. For example, it will be apparent to those skilled in the art that various other types of circuit configurations relating to cuff pressurization and the like could be employed in accordance with the invention. It will be further apparent to those skilled in the art that modifications and variations of the above-described illustrative embodiment of the invention may be effected without departing from the spirit and scope of the novel concepts of the invention.

The embodiments of the invention in which an exclusive property or privilege is claimed are defined as follows:

1. An oscillometric blood pressure device for measuring systolic and diastolic blood pressures, and adapted to be interconnected to a cuff attachable to a test subject, said blood pressure device comprising:
    means adapted to be coupled to said cuff for applying an occluding pressure greater than said systolic pressure in the vicinity of an artery of said test subject;
    means adapted to be coupled to said cuff for decreasing said occluding pressure to a pressure below said diastolic pressure;
    a pressure transducer adapted to be coupled to said cuff for generating analog pressure signals representative of instantaneous cuff pressure, said analog pressure signals comprising a first analog signal representative of blood pressure pulses occurring in said artery, and a second analog signal representative of static cuff pressure;
    circuit means responsive to said first analog signal for generating, for each of said blood pressure pulses, a difference measurement indicative of the difference between a peak amplitude of a pulse and an integral of said pulse, so that for a plurality of said blood pressure pulses, said circuit means generates a plurality of difference measurements; and said circuit means generates signals indicating values of said systolic pressure and said diastolic pressure based on said difference measurements.

2. An oscillometric blood pressure device in accordance with claim 1 characterized in that said circuit means generates said signals indicating a value of said systolic pressure substantially near the time of occurrence of a blood pressure pulse having a difference measurement indicating that the static cuff pressure occurring near the time of occurrence of said pulse substantially corresponds to said systolic pressure.

3. An oscillometric blood pressure device in accordance with claim 1 characterized in that said circuit means generates said signals indicating a value of said diastolic pressure substantially near the time of occurrence of a blood pressure pulse having a difference measurement indicating that the static cuff pressure occurring near the time of occurrence of said pulse substantially corresponds to said diastolic pressure.

4. An oscillometric blood pressure device in accordance with claim 1 characterized in that said circuit means generates said signals indicating a value of said systolic pressure prior to the time of occurrence of said diastolic pressure.

5. An oscillometric blood pressure device in accordance with claim 1 characterized in that said circuit means is further responsive to said analog signals for generating signals indicating the value of mean arterial pressure.

6. An oscillometric blood pressure device in accordance with claim 1 characterized in that said circuit means comprises means for periodically sampling said analog signals, in the absence of the occurrence of a blood pressure pulse, and for generating signals indicating values of said static cuff pressure.

7. An oscillometric blood pressure device in accordance with claim 1 characterized in that said circuit means comprises means for detecting the occurrence of a blood pressure pulse having an amplitude greater than a reference threshold value.

8. An oscillometric blood pressure device in accordance with claim 1 characterized in that said circuit means generates said signals indicating the values of said systolic pressure and said diastolic pressure based on magnitudes of difference measurements of blood pressure pulses relative to magnitudes of difference measurements of immediately previously occurring blood pressure pulses.

9. An oscillometric blood pressure device in accordance with claim 1 characterized in that said circuit means generates said signals indicating a value for said systolic pressure on the basis of an identification of the occurrence of a valid group of blood pressure pulses when a predetermined number of successive difference measurements increase in magnitude.

10. An oscillometric blood pressure device in accordance with claim 1 characterized in that said circuit means generates said signals indicating a value for said diastolic pressure on the basis of an identification of the occurrence of a valid group of blood pressure pulses when a predetermined number of successive difference measurements decrease in magnitude.

11. An oscillometric blood pressure device in accordance with claim 1 characterized in that said circuit means comprises pulse detection means responsive to said first analog signal for generating a pulse detection signal indicative of the occurrence of a blood pressure pulse.

12. An oscillometric blood pressure device in accordance with claim 1 characterized in that said circuit means comprises peak detection means responsive to said first analog signal for generating, for each of said blood pressure pulses, a peak detection signal indicative of a peak amplitude of each of said pulses.

13. An oscillometric blood pressure device in accordance with claim 1 characterized in that said circuit means comprises pulse integration means responsive to said first analog signal for generating, for each of said blood pressure pulses, a pulse integral signal indicative of an integral of each of said pulses.

14. An oscillometric blood pressure device in accordance with claim 1 characterized in that said circuit means comprises:

pulse detection means responsive to said first analog signal for generating a pulse detection signal indicative of the occurrence of a blood pressure pulse;

peak detection means responsive to said first analog signal for generating a peak detection signal indicative of the peak amplitude of said blood pressure pulse;

pulse integration means responsive to said first analog signal for generating a pulse integral signal indicative of the integral of said pulse; and differencing means responsive to said peak amplitude signal and to said pulse integral signal for generating, for each blood pressure pulse detected by said pulse detection means, said difference measurement, wherein said difference measurement represents a value of said peak amplitude signal subtracted from the value of said pulse integral signal.

15. An oscillometric blood pressure device in accordance with claim 1 characterized in that said circuit means comprises analog-to-digital conversion means for converting said peak amplitude signal into a digital peak amplitude signal, and for converting said pulse integral signal into a digital pulse integral signal.

16. An oscillometric blood pressure device in accordance with claim 14 characterized in that said circuit means further comprises means for periodically sampling said analog signals, in the absence of the occurrence of a blood pressure pulse, and for storing a signal representative of the most recent sample of said analog signals occurring prior to the time of the occurrence of a blood pressure pulse.

17. An oscillometric blood pressure device in accordance with claim 1 characterized in that said circuit means comprises:

first filter means responsive to said analog pressure signals for filtering said first analog signal and for generating only said second analog signal representative of said static cuff pressure.

18. An oscillometric blood pressure device in accordance with claim 17 characterized in that said circuit means further comprises a differencing circuit responsive to said analog pressure signals for subtracting said second analog signal from said analog pressure signals, and for generating only said first analog signal.

19. An oscillometric blood pressure device in accordance with claim 1 characterized in that said device further comprises display means responsive to said signals indicating values of said systolic pressure and said diastolic pressure for providing a visual display of said systolic pressure and said diastolic pressure.

20. An oscillometric blood pressure device for measuring systolic and diastolic blood pressures, and adapted to be interconnected to a cuff attachable to a test subject, said blood pressure device comprising:

means adapted to be coupled to said cuff for applying an occluding pressure greater than said systolic pressure in the vicinity of an artery of said test subject;

means adapted to be coupled to said cuff for decreasing said occluding pressure to a pressure below said diastolic pressure;

a pressure transducer adapted to be coupled to said cuff for generating analog pressure signals representative of instantaneous cuff pressure, said analog pressure signals comprising a first analog signal representative of blood pressure pulses occurring in said artery, and a second analog signal representative of static cuff pressure;

an analog pulse detection circuit responsive to said first analog signal for generating an analog pulse detection output signal having a first state indicative of the occurrence of a pulse and a second state indicative of the absence of a pulse;

an analog peak detection circuit responsive to said first analog signal for generating an analog peak amplitude signal representative of the maximum amplitude of each pulse;

an analog integrator circuit responsive to said first analog signal for generating an analog integral signal representative of the integral of each pulse;

circuit means responsive to said analog pulse detector output signal, said analog peak amplitude signal and said analog integral signal for generating, for each of said blood pressure pulses, a difference measurement indicative of the difference between a peak amplitude of a pulse and an integral of said pulse, so that for a plurality of said blood pressure pulses, said circuit means generates a plurality of difference measurements; and said circuit means generates signals indicating values of said systolic pressure and said diastolic pressure based on said difference measurements.

21. An oscillometric blood pressure device in accordance with claim 20 characterized in that said signals indicating values of said systolic pressure are generated when a predetermined number of successive difference measurements increase in amplitude.

22. An oscillometric blood pressure device in accordance with claim 20 characterized in that said signals indicating values of said diastolic pressure are generated when a predetermined number of successive difference measurements decrease in amplitude.

23. An oscillometric blood pressure device in accordance with claim 20 characterized in that said circuit means comprises conversion means for converting said analog peak amplitude signal into a digital peak amplitude signal, and for converting said analog pulse integral signal into a digital pulse integral signal.

24. An oscillometric blood pressure device in accordance with claim 23 characterized in that said circuit means further comprises:

processing means responsive to said digital peak amplitude signal and to said digital pulse integral signal for generating, for each of said blood pressure pulses, digital signals representative of the difference between said digital peak amplitude signal and said digital pulse integral signal.

25. An oscillometric blood pressure device for measuring systolic and diastolic blood pressures, and adapted to be interconnected to a cuff attachable to a test subject, said blood pressure device comprising:

pump means adapted to be coupled to said cuff for applying an occluding pressure greater than said systolic pressure in the vicinity of an artery of said test subject;

bleed means adapted to be coupled to said cuff for decreasing said occluding pressure to a pressure below said diastolic pressure;

transducer means coupled to said cuff for generating an analog pressure signals representative of instantaneous cuff pressure, said analog pressure signal comprising a first analog signal representative of blood pressure pulses occurring in said artery and a second analog signal representative of static cuff pressure;

first filter means responsive to said analog pressure signal for filtering said analog pressure signal and generating only said second analog signal;

differencing circuit means responsive to said analog pressure signal and said second analog signal generated by said filter means for generating an output signal comprising said first analog signal superimposed on a DC level signal;

second filter means responsive to said output signal from said differencing circuit means for removing said DC component and for generating only said first analog signal;

reference threshold means for generating a reference threshold signal;

pulse detector means responsive to said first analog signal and said reference threshold single for generating a pulse detection signal having a first state when said first analog signal is greater than said reference threshold signal, and a second state when said first analog signal is less than said reference threshold signal;

reset control means responsive to said pulse detector means for generating a reset signal depending on the state of said pulse detector signal;

integrator means responsive to said first analog signal and to said reset signal for integrating said first analog signal during the occurrence of a pulse;

peak detector means responsive to said first analog signal and to said reset signal for generating a peak amplitude signal indicative of the peak amplitude occurring during a pulse;

processing means responsive to said pulse detector signal for generating control signals;

sampling means responsive to said peak detector signal, said integrator signal, said analog signal and said control signals for selectively generating digital representations of said peak amplitude signal, said integrator signal and said second analog signal;

said processor means is responsive to said digital representations of said peak detector signal, said integrator signal and said second analog signal for generating, for each of said blood pressure pulses, a difference measurement indicative of the difference between a peak amplitude of a pulse and the integral of said pulse, so that for a plurality of said blood pressure pulses, said circuit means generates a plurality of difference measurements; and said processing means generates signals indicating values of said systolic pressure and said diastolic pressure based on said difference measurements.

26. An oscillometric device having means to detected the occurrence of pulses in an analog electrical signal, means for generating pulse characteristic signals representative of predetermined characteristics of said pulses, and means for analyzing characteristics of said pulses and for generating indicating signals on the basis of said analysis of said pulse characteristics, the improvement comprising:

filter means responsive to said analog signal for filtering said analog signal and for generating a filtered analog signal representative only of said pulses, wherein said pulse characteristics generating means is responsive to said filtered analog signal for generating analog pulse characteristic signals representative of predetermined characteristics of each of said pulses, said pulse characteristic signals each having a steady state value substantially at the time of occurrence of the end of a pulse; and said analyzing means comprises means responsive to said detection means detecting the end of a pulse for sampling, only once for each detected pulse, each of said pulse characteristic signals and for generating said indicating signals on the basis of an analysis of said sampled pulse characteristic signals, so that said indicating signals can be generated without requiring any periodic sampling of said pulse characteristic signals or said filtered analog signal during the occurrence of pulses.

27. An oscillometric blood pressure device for measuring systolic and diastolic blood pressures, and adapted to be interconnected to a cuff attachable to a test subject, said blood pressure device comprising:

means adapted to be coupled to said cuff for applying an occluding pressure greater than said systolic pressure in the vicinity of an artery of said test subject;

means adapted to be coupled to said cuff for decreasing said occluding pressure to a pressure below said diastolic pressure;

a pressure transducer adapted to be coupled to said cuff for generating analog pressure signals representative of instantaneous cuff pressure, said analog pressure signals comprising a first analog signal representative of blood pressure pulses occurring in said artery, and a second analog signal representative of static cuff pressure;

filter means responsive to said analog pressure signals for filtering said analog pressure signals and for generating a filtered analog signal comprising said first analog signal;

pulse characteristic generating means responsive to said filtered analog signal for generating analog pulse characteristic signals representative of predetermined characteristics of each of said pulses, said pulse characteristic signals each having a steady state value substantially at the time of occurrence of the end of a pulse;

pulse detection means responsive to said filtered analog signal for detecting the occurrence of a pulse, including the end of a pulse; and analyzing means responsive to said detection means detecting the end of a pulse for sampling, only once for each detected pulse, each of said pulse characteristic signals and for generating indicating signals on the basis of an analysis of said sampled pulse characteristic signals, said indicating signals indicating the occurrence or non-occurrence of said systolic and diastolic blood pressures, wherein said indicating signals are generated without requiring any periodic sampling of said pulse characteristic signals or said filtered analog signal during the occurrence of pulses.

28. A method adapted for use with an oscillometric blood pressure device for measuring systolic and diastolic blood pressures, said method comprising the steps of:

applying to a cuff attachable to a test subject an occluding pressure greater than said systolic pressure in the vicinity of an artery of said test subject;

gradually decreasing said occluding pressure;

generating analog pressure signals representative of instantaneous cuff pressure, with said analog pressure signals comprising a first analog signal representative of blood pressure pulses occurring in said artery and a second analog signal representative of static cuff pressure;

generating, for each of said blood pressure pulses, and in response to said first analog signal, a difference measurement indicative of the difference between a peak amplitude of a pulse and an integral of said pulse, so that for a plurality of said blood pressure pulses, a plurality of difference measurements are generated; and generating signals indicating values of said systolic pressure and said diastolic pressure based on said difference measurements.

29. A method in accordance with claim 28, further comprising the step of generating said signals indicating a value of said systolic pressure substantially near the time of occurrence of a blood pressure pulse having a difference measurement indicating that the static cuff pressure occurring near the time of occurrence of said pulse substantially corresponds to said systolic pressure.

30. A method in accordance with claim 28, characterized in that said method further comprises the step of generating said signals indicating a value of said diastolic pressure substantially near the time of occurrence of a blood pressure pulse having a difference measurement indicating that the static cuff pressure occurring near the time of occurrence of said pulse substantially corresponds to said diastolic pressure.

31. A method in accordance with claim 28 characterized in that said method further comprises the step of generating, in response to said analog signals, signals indicating the value of mean arterial pressure.

32. A method in accordance with claim 28 characterized in that said method further comprises the step of periodically sampling said analog signals, in the absence of the occurrence of a blood pressure pulse, and generating signals indicating values of said static cuff pressure.

33. A method in accordance with claim 28 characterized in that said method further comprises the step of generating said signals indicating values of said systolic pressure and said diastolic pressure based on magnitudes of difference measurements of blood pressure pulses relative to magnitudes of difference measurements of immediately previously occurring blood pressure pulses.

* * * * *

UNITED STATES PATENT AND TRADEMARK OFFICE
CERTIFICATE OF CORRECTION

PATENT NO. : 5,054,494
DATED : October 08, 1991
INVENTOR(S) : GERARD M. LAZZARO ET AL It is certified that error appears in the above–identified patent and that said Letters Patent is hereby corrected as shown below:

The Title page should be deleted to appear as per attached title page.

The drawing sheets consisting of Figures 2 and 9 should be deleted to appear as per attached sheets.

Col. 39, Claim 26, Line 1, "detected" should be --detect--.

Col. 39, Claim 26, Line 12, "characteristics" should be --characteristic--.

Signed and Sealed this

Twelfth Day of October, 1993

Attest:

BRUCE LEHMAN

*Attesting Officer*  *Commissioner of Patents and Trademarks*

United States Patent [19]

Lazzaro et al.

[11] Patent Number: 5,054,494
[45] Date of Patent: Oct. 8, 1991

[54] OSCILLOMETRIC BLOOD PRESSURE DEVICE

[75] Inventors: Gerard M. Lazzaro, Bethlehem; Raymond J. Huey, Stratford, both of Conn.

[73] Assignee: U.S. Medical Corporation, Cheshire, Conn.

[21] Appl. No.: 456,768

[22] Filed: Dec. 26, 1989

[51] Int. Cl.⁵ .................................................. A61B 5/02
[52] U.S. Cl. ............................... 128/677; 128/681; 128/683; 128/687
[58] Field of Search ............... 128/677, 680, 681, 682, 128/683, 687

[56] References Cited

U.S. PATENT DOCUMENTS

| | | | |
|---|---|---|---|
| 3,315,662 | 4/1967 | Buffington | 128/681 |
| 3,738,356 | 6/1973 | Workman | 28/675 |
| 3,765,405 | 10/1973 | Natkanski | 128/680 |
| 3,894,535 | 7/1975 | Cannon et al. | 128/672 |
| 4,137,907 | 2/1979 | Jansen et al. | 128/681 |
| 4,154,238 | 5/1979 | Link | 128/681 |
| 4,159,111 | 6/1979 | Lowth | 128/25 |
| 4,206,765 | 6/1980 | Huber | 128/677 |
| 4,211,238 | 7/1980 | Shu et al. | 128/700 |
| 4,216,779 | 8/1980 | Squires et al. | 128/682 |
| 4,252,127 | 2/1981 | Gemelke | 128/680 |
| 4,258,430 | 3/1981 | Tyburski | 364/900 |
| 4,263,918 | 4/1981 | Swearingen et al. | 128/681 |
| 4,326,569 | 4/1982 | Vaillancourt | 141/383 |
| 4,344,421 | 8/1982 | Bareiss | 28/24 |
| 4,356,827 | 11/1982 | Uemura et al. | 128/680 |
| 4,361,877 | 11/1982 | Dyer et al. | 364/900 |
| 4,378,807 | 4/1983 | Peterson et al. | 128/680 |
| 4,400,783 | 8/1983 | Locke, Jr. et al. | 364/483 |
| 4,407,297 | 10/1983 | Croslin | 128/681 |
| 4,417,306 | 11/1983 | Citron et al. | 364/415 |
| 4,417,587 | 11/1983 | Ichinomiya et al. | 128/682 |
| 4,420,819 | 12/1983 | Price et al. | 364/900 |
| 4,429,700 | 2/1984 | Thees et al. | 128/681 |
| 4,461,266 | 7/1984 | Hood, Jr. et al. | 128/681 |
| 4,464,123 | 8/1984 | Glover et al. | 128/681 |
| 4,466,879 | 8/1984 | Ho et al. | 204/415 |
| 4,501,280 | 2/1985 | Hood, Jr. | 128/677 |
| 4,519,398 | 5/1985 | Lisiecki et al. | 128/710 |
| 4,543,963 | 10/1985 | Medero et al. | 128/682 |
| 4,546,775 | 10/1985 | Medero | 128/681 |
| 4,576,180 | 3/1986 | Taheri | 128/673 |
| 4,592,018 | 5/1986 | Wiegman | 365/63 |
| 4,592,366 | 6/1986 | Sainomoto et al. | 128/680 |
| 4,608,994 | 9/1986 | Ozawa et al. | 128/670 |
| 4,617,937 | 10/1986 | Peel et al. | 128/680 |
| 4,618,929 | 10/1986 | Miller et al. | 364/415 |
| 4,627,440 | 12/1986 | Ramsey, III et al. | 128/682 |
| 4,634,982 | 1/1987 | Pungor et al. | 324/448 |
| 4,638,810 | 1/1987 | Ramsey, III et al. | 128/681 |
| 4,653,506 | 3/1987 | Romanovskaya | 28/685 |
| 4,660,566 | 4/1987 | Palti | 128/677 |
| 4,677,983 | 7/1987 | Yamaguchi et al. | 128/680 |
| 4,690,151 | 9/1987 | Utsunomiya et al. | 128/682 |
| 4,699,152 | 10/1987 | Link | 128/677 |
| 4,706,684 | 11/1977 | Sorensen et al. | 128/677 |
| 4,712,563 | 12/1987 | Link | 128/681 |
| 4,712,564 | 12/1987 | Yamaguchi | 128/682 |
| 4,716,906 | 1/1988 | Ruff | 128/686 |
| 4,717,885 | 3/1988 | Ruff | 128/686 |

(List continued on next page.)

Primary Examiner—Francis Jaworski
Assistant Examiner—George Manuel
Attorney, Agent, or Firm—Varnum, Riddering, Schmidt & Howlett

[57] ABSTRACT

An oscillometric blood pressure measuring device (200) is disclosed for determining systolic, mean and diastolic blood pressures. The device (200) includes a cuff (202) adapted to be continuously deflated during a measuring cycle. Analog signals representative of pulsatile changes in cuff pressure are utilized to generate signals representative of pulse characteristics, including peak amplitude and pulse integral characteristics. Difference signals are then generated for the pulses, representative of the difference between peak amplitudes and pulse integrals, and a determination is made as to the systolic and diastolic blood pressure based on these difference signals and static cuff pressures.

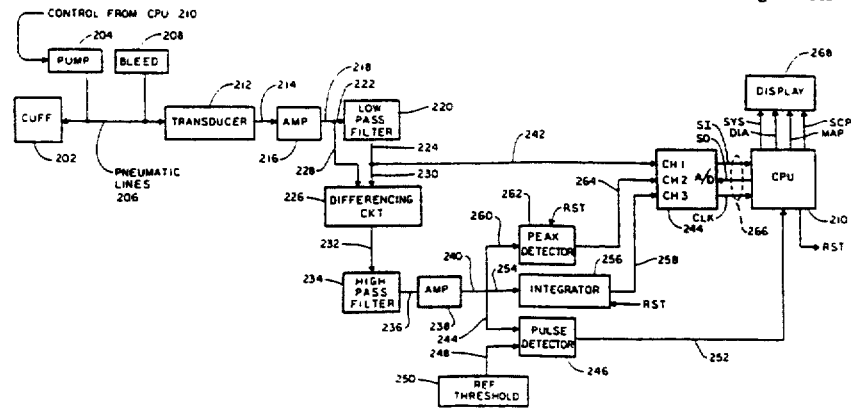

33 Claims, 10 Drawing Sheets